(12) United States Patent
Aizawa et al.

(10) Patent No.: US 10,036,750 B2
(45) Date of Patent: Jul. 31, 2018

(54) IMMUNOCHROMATOGRAPHY, AND DETECTION DEVICE AND REAGENT FOR THE SAME

(71) Applicant: FURUKAWA ELECTRIC CO., LTD., Tokyo (JP)

(72) Inventors: Hideki Aizawa, Tokyo (JP); Michio Ohkubo, Tokyo (JP); Kazutomi Miyoshi, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 392 days.

(21) Appl. No.: 14/674,825

(22) Filed: Mar. 31, 2015

(65) Prior Publication Data

US 2015/0268239 A1  Sep. 24, 2015

Related U.S. Application Data

(63) Continuation of application No. PCT/JP2013/081913, filed on Nov. 27, 2013.

(30) Foreign Application Priority Data

Nov. 28, 2012  (JP) ................................. 2012-260227

(51) Int. Cl.
G01N 33/558 (2006.01)
G01N 33/569 (2006.01)
(Continued)

(52) U.S. Cl.
CPC ....... *G01N 33/56983* (2013.01); *G01N 21/59* (2013.01); *G01N 21/6428* (2013.01);
(Continued)

(58) Field of Classification Search
USPC ....... 435/7.1, 7.92, 7.95, 970, 973; 436/172, 436/169, 514, 164, 546, 800, 805;
(Continued)

(56) References Cited

U.S. PATENT DOCUMENTS 7,955,866 B2   6/2011  Aizawa et al.
2005/0044394 A1  2/2005  Wang
(Continued)

FOREIGN PATENT DOCUMENTS

CN   1563951 A   1/2005
CN   2779402 Y   5/2006
(Continued)

OTHER PUBLICATIONS

Chinese Office Action and Search Report, dated Jan. 6, 2016, for Chinese Application No. 201380037337.3, including English translation.
(Continued)

*Primary Examiner* — Erik B Crawford
(74) *Attorney, Agent, or Firm* — Birch, Stewart, Kolasch & Birch, LLP

(57) ABSTRACT

An immunochromatography for multi-item detection is provided which contains detecting and measuring fluorescence and light absorption respectively at once with a detection device. The immunochromatography contains using fluorescent particles and light absorbing particles, wherein the fluorescence excitation wavelength of the fluorescent particles and the absorption wavelength of the light absorbing particles are in the same wavelength region; and detecting and measuring, at once, the intensity of reflected light from a test area, the intensity of reflected light from another test area, and the intensity of reflected light from a non-test area other than the test areas.

7 Claims, 4 Drawing Sheets

(51) Int. Cl.
*G01N 21/59* (2006.01)
*G01N 21/64* (2006.01)
*G01N 33/58* (2006.01)
*G01N 21/84* (2006.01)
*B82Y 30/00* (2011.01)

(52) U.S. Cl.
CPC ....... *G01N 21/8483* (2013.01); *G01N 33/558* (2013.01); *G01N 33/582* (2013.01); *B82Y 30/00* (2013.01); *G01N 21/6489* (2013.01); *G01N 2021/6439* (2013.01); *G01N 2021/8488* (2013.01); *G01N 2333/08* (2013.01); *G01N 2333/11* (2013.01); *G01N 2469/10* (2013.01)

(58) Field of Classification Search
USPC .......................................... 422/82.05, 82.09
See application file for complete search history.

(56) References Cited

U.S. PATENT DOCUMENTS

| | | |
|---|---|---|
| 2005/0249633 A1 | 11/2005 | Blatt et al. |
| 2006/0041058 A1 | 2/2006 | Yin et al. |
| 2009/0017561 A1 | 1/2009 | Aizawa et al. |
| 2009/0068639 A1 | 3/2009 | Aizawa et al. |
| 2009/0215096 A1 | 8/2009 | Aizawa et al. |
| 2009/0305290 A1 | 12/2009 | Sambursky et al. |

FOREIGN PATENT DOCUMENTS

| | | |
|---|---|---|
| CN | 1936540 A | 3/2007 |
| CN | 101017168 A | 8/2007 |
| CN | 101187665 A | 5/2008 |
| CN | 102004146 A | 4/2011 |
| CN | 102520180 A | 6/2012 |
| JP | 61-62865 A | 3/1986 |
| JP | 2001-33454 A | 2/2001 |
| JP | 2006-38700 A | 2/2006 |
| JP | 2007-512533 A | 5/2007 |
| JP | 2009-115822 A | 5/2009 |
| JP | 2010-14631 A | 1/2010 |
| JP | 2010-197248 A | 9/2010 |
| JP | 2011-214858 A | 10/2011 |
| JP | 2011-220705 A | 11/2011 |
| JP | 2011-528229 A | 11/2011 |
| JP | 2013-53869 A | 3/2013 |
| WO | WO 2007/097377 A1 | 8/2007 |
| WO | WO 2008/018566 A1 | 2/2008 |

OTHER PUBLICATIONS

Extended European Search Report for European Application No. 13859219.1, dated Jun. 23, 2016.
Chinese Office Action and Search Report for Chinese Application No. 201380037337.3, dated Aug. 12, 2015, with an English translation.
Taiwan Office Action for Appl. No. 102143429 dated Apr. 13, 2015 (w/ English translation).
International Search Report, dated Feb. 4, 2014, issued in PCT/JP2013/081913.

Fig. 1
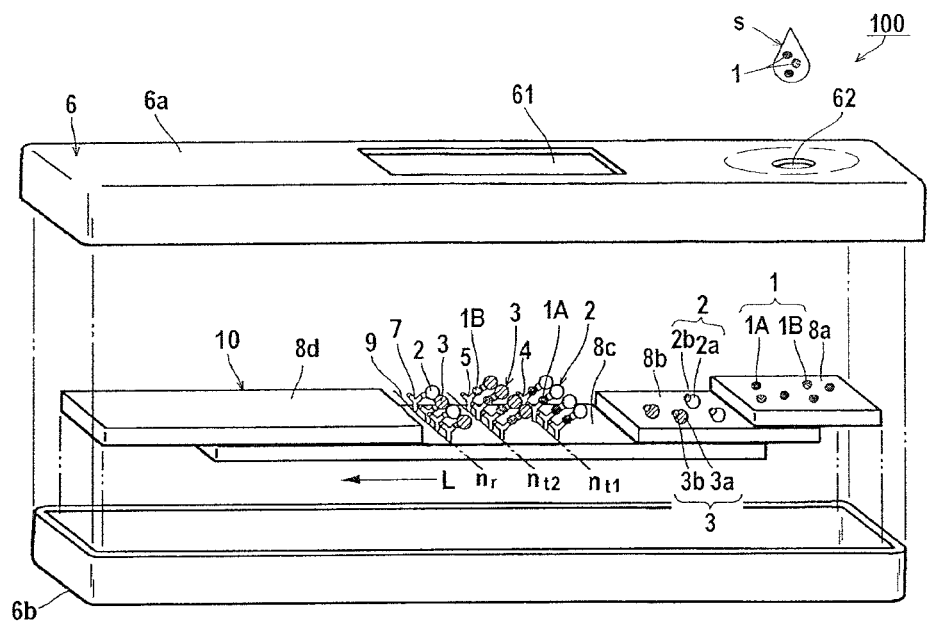
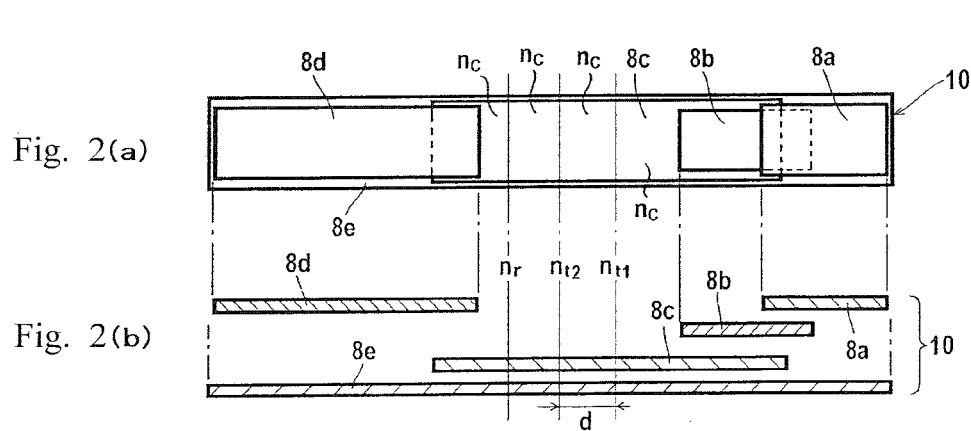
Fig. 2(a)
Fig. 2(b)

IMMUNOCHROMATOGRAPHY, AND DETECTION DEVICE AND REAGENT FOR THE SAME

CROSS-REFERENCE TO RELATED APPLICATIONS

This application is a Continuation of PCT International Application No. PCT/JP2013/081913 filed on Nov. 27, 2013, which claims priority under 35 U.S.C. § 119 (a) to Japanese Patent Application No. 2012-260227 filed on Nov. 28, 2012. Each of the above applications is hereby expressly incorporated by reference, in its entirety, into the present application.

TECHNICAL FIELD

The present invention relates to an immunochromatography, and a detection device and a reagent for the same.

BACKGROUND ART

An immunochromatography is a diagnostic method using nanoparticles. Being simple to operate and requiring relatively short time of approximately 5 to 30 minutes for determination and no expensive devices, it is widely used as an excellent simple diagnostic method in actual clinical scenes. For example, for determination of influenza virus infection, by having a pharynx cotton swab or nasal cavity cotton swab collected from a patient as an analyte, the determination can be made on site within a short time, and thus it is used as a very dominant tool for quick determination of infection.

Colored particles such as gold colloid or colored latex particles are generally used as labeling particles for the immunochromatography. In some cases, the sensitivity of immunochromatography using such colored particles is insufficient, depending on the condition or amount of the analyte or the measurement item. Moreover, the result may be false positive or false negative, which can be a cause of misdiagnosis and the like. For solving these problems, it has been tried to achieve highly sensitive immunochromatography.

The applicant has proposed methods for increasing the sensitivity of immunochromatography, which include fluorescent immunochromatography using fluorescent particles or using fluorescent particles in combination with light absorbing particles (see Patent Literatures 1 to 3). Using the proposed techniques, fluorescence emitted from the test area can be detected not only visually but also with an optical receiver for high accuracy or convenience of quantitative measurement. For a high-sensitivity detection device suitable for use in this measurement, the applicant has previously proposed a technique using a specific lens system as disclosed in Patent Literature 4.

CITATION LIST

Patent Literatures

Patent Literature 1: WO 2008/018566
Patent Literature 2: WO 2007/097377
Patent Literature 3: JP-A-2010-14631 ("JP-A" means unexamined published Japanese patent application)
Patent Literature 4: JP-A-2010-197248

SUMMARY OF INVENTION

Technical Problem

On the other hand, the applicant has developed an immunochromatographic technique for multi-item detection, in which different target substances are captured and detected using a reagent including a combination of fluorescent particles and light absorbing particles (note that Patent Literature 3 discloses a single item detection technique in which a single target substance is captured using fluorescent particles and light absorbing particles). For example, this technique can make it possible to diagnose two or more different diseases, infectious items, or other items at once in medical sites, so that the efficiency of immunochromatographic tests can be significantly improved. There has been no technical development based on such an idea about the use of a combination of fluorescence and light absorption. In addition, no studies have been conducted on methods and devices for such detection.

Under these circumstances, the present invention contemplates providing a method and a device capable of detecting and measuring fluorescence and light absorption at once in immunochromatography using a combination of fluorescent particles and light absorbing particles, which are designed to capture different target substances, respectively.

Solution to Problem

According to the present invention, the problems are solved by the following means.
[1] An immunochromatography for multi-item detection, containing steps of:
  applying, to a test piece having fluorescent particles and light absorbing particles as labeling particles, a liquid sample suspected of containing target substances A and B, so that the fluorescent particles and the light absorbing particles are allowed to flow; and
  detecting and measuring fluorescence and light absorption respectively at once with a detection device,
  wherein the fluorescence is derived from the fluorescent particles captured in a test area of the test piece, and the light absorption is derived from the light absorbing particles captured in another test area of the test piece,
  wherein the detection device contains a detection unit for detecting fluorescence and light absorption, and a control unit for controlling the detection unit,
  wherein the fluorescent particles and the light absorbing particles are such that the fluorescent particles have a fluorescence excitation wavelength ($\lambda_1$), the light absorbing particles have an absorption wavelength ($\lambda_2$), the fluorescence excitation wavelength ($\lambda_1$) and the absorption wavelength ($\lambda_2$) are in the same wavelength region, the target substance A is captured by the fluorescent particles when detected, the target substance B is captured by the light absorbing particles when detected, and the target substance A and the target substance B are different from each other,
  wherein the test area $n_{f1}$ where the fluorescent particles are captured and the test area $n_{f2}$ where the light absorbing particles are captured each are provided with the test piece at different positions, and
  wherein the control unit of the detection device commands the detection unit to scan the test piece and to detect and measure, at once, the intensity of reflected light from the test area $n_{f1}$, the intensity of reflected light from the test area $n_{t2}$, and the intensity of reflected light from a non-test area other than the test areas $n_{t1}$ and $n_{t2}$.

[2] The immunochromatography according to the above item [1],
wherein the detection device has means for read-out and analysis, and
wherein the means for read-out and analysis detects the target substances by the fact that the intensity of reflected light from the test area $n_{t1}$ where the fluorescent particles are captured is higher than the intensity of reflected light from the non-test area and by the fact that the intensity of reflected light from the test area $n_{t2}$ where the light absorbing particles are captured is lower than the intensity of reflected light from the non-test area.

[3] The immunochromatography according to the above item [1] or [2], wherein the light absorbing particles are gold colloid particles, colored silica particles, or colored latex particles.

[4] The immunochromatography according to any one of the above items [1] to [3], wherein the fluorescence excitation wavelength ($\lambda_1$) and the light absorption wavelength ($\lambda_2$) are in the range of from 300 nm to 800 nm.

[5] The immunochromatography according to any one of the above items [1] to [4], wherein the distance between the test areas $n_{t1}$ and $n_{t2}$ is in the range of from 1 mm to 10 mm.

[6] The immunochromatography according to any one of the above items [1] to [5], wherein the target substances are quantified from the area of a peak corresponding to the fluorescence excitation wavelength and/or the area of a peak corresponding to the light absorption wavelength.

[7] The immunochromatography according to any one of the above items [1] to [6], wherein the intensity of reflected light from the test area $n_{t1}$ where the fluorescent particles are captured, the intensity of reflected light from the test area $n_{t2}$ where the light absorbing particles are captured, and the intensity of reflected light from the non-test area are all detected by a single optical receiver provided with the detection unit.

[8] The immunochromatography according to any one of the above items [1] to [7],
wherein for the sample suspected of containing the target substances A and B,
the presence of the target substance A is determined by the fact that the intensity of reflected light from the test area $n_{t1}$ is higher than the intensity of reflected light from the non-test area,
the presence of the target substance B is determined by the fact that the intensity of reflected light from the test area $n_{t2}$ is lower than the intensity of reflected light from the non-test area,
the absence of both substances is determined by the fact that the intensity of reflected light from the test area $n_{t1}$, the intensity of reflected light from the test area $n_{t2}$, and the intensity of reflected light from the non-test area are at substantially the same level, and
the presence of both substances is determined by the fact that the intensity of reflected light from the test area $n_{t1}$ is higher than the intensity of reflected light from the non-test area, and the fact that the intensity of reflected light from the test area $n_{t2}$ is lower than the intensity of reflected light from the non-test area.

[9] A detection device for performing an immunochromatography for multi-item detection, containing:
applying, to a test piece having fluorescent particles and light absorbing particles as labeling particles, a liquid sample suspected of containing target substances A and B, so that the fluorescent particles and the light absorbing particles are allowed to flow, and
detecting and measuring, at once, the intensity of reflected light from a test area $n_{t1}$ of the test piece where the fluorescent particles are captured, the intensity of reflected light from a test area $n_{t2}$ of the test piece where the light absorbing particles are captured, and the intensity of reflected light from a non-test area other than the test areas $n_{t1}$ and $n_{t2}$,
wherein the detection device contains a detection unit for detecting fluorescence and light absorption, and a control unit for controlling the detection unit, and wherein the control unit of the detection device is configured to command the detection unit to scan the test piece and to detect and measure, at once, the intensity of reflected light from the test area $n_{t1}$, the intensity of reflected light from the test area $n_{t2}$, and the intensity of reflected light from the non-test area under conditions satisfying the following requirements (i) to (iii):
(i) the fluorescent excitation wavelength of the fluorescent particles and the absorption wavelength of the light absorbing particles are in the same wavelength region;
(ii) the target substance A and the target substance B are different from each other; and
(iii) the test area $n_{t1}$ and the test area $n_{t2}$ are provided with the test piece at different positions.

[10] The detection device according to the above item [9], further containing means for read-out and analysis,
wherein the means for read-out and analysis is configured
to determine the presence of the target substance A by the fact that the intensity of reflected light from the test area $n_{t1}$ is higher than the intensity of reflected light from the non-test area,
to determine the presence of the target substance B by the fact that the intensity of reflected light from the test area $n_{t2}$ is lower than the intensity of reflected light from the non-test area,
to determine the absence of both substances by the fact that the intensity of reflected light from the test area $n_{t1}$, the intensity of reflected light from the test area $n_{t2}$, and the intensity of reflected light from the non-test area are at substantially the same level, and
to determine the presence of both substances by the fact that the intensity of reflected light from the test area $n_{t1}$ is higher than the intensity of reflected light from the non-test area, and the fact that the intensity of reflected light from the test area $n_{t2}$ is lower than the intensity of reflected light from the non-test area.

[11] The detection device according to the above item [9] or [10], wherein an optical receiver incorporated in the detection unit of the detection device has light sensitivity in a wavelength region where the light absorption and the fluorescence are to be detected.

[12] An immunochromatographic reagent for use in the immunochromatography according to any one of the above items [1] to [8], containing fluorescent particles and light absorbing particles,
wherein a binding substance for capturing a target substance A is incorporated into the fluorescent particles, and
wherein a binding substance for capturing a target substance B different from the target substance A is incorporated into the light absorbing particles.

As used herein, the term "detecting and measuring at once" means that a plurality of items are detected and measured with a single device without switching from the device to another device. A plurality of items does not need to be detected and measured simultaneously. However, they are preferably detected and measured around the same time (preferably within 30 seconds, more preferably within 10 seconds). Typically, the term means that the detection and the measurement can be performed by single scanning with the detection unit.

Advantageous Effects of Invention

In immunochromatography using a combination of fluorescent particles and light absorbing particles for capturing different target substances, respectively, the immunochromatography and detection device of the present invention makes it possible to detect and measure the fluorescence and the light absorption at once. The detection and measurement of the fluorescence and the light absorption at once allows efficient detection and measurement of a plurality of target substances, which makes it possible to significantly improve the efficiency of immunochromatographic tests for diagnosis and treatment. The detection device of the present invention makes it possible to detect fluorescence and light absorption at once with a single detection unit, so that it can contribute to space saving and device cost reduction for immunochromatography.

In the immunochromatography of the present invention, silica particles or latex particles can be used as reagent particles (specifically fluorescent particles). Silica is a material having a light transmittance higher than that of latex particles. When silica particles are used for fluorescent particles, light from a light source can efficiently enter and pass through the inside of the silica particles, so that a dye in the silica particles can be efficiently excited. In the case of fluorescent particles, light can efficiently excite the dye in the silica particles. In the case of light absorbing particles, a dye in the silica particles can efficiently absorb light from a light source. Therefore, silica can produce more advantageous effects.

Other and further features and advantages of the invention will appear more fully from the following description, appropriately referring to the accompanying drawings.

BRIEF DESCRIPTION OF DRAWINGS

FIG. 1 is an exploded perspective view schematically illustrating the long test stick that can be preferably used in the present invention.

FIGS. 2(a) and 2(b) are diagrams illustrating the immunochromatography test piece that can be preferably used in the present invention, in which FIG. 2(a) is a plan view and FIG. 2(b) is an expanded cross-sectional view.

DESCRIPTION OF EMBODIMENTS

Figure 3:
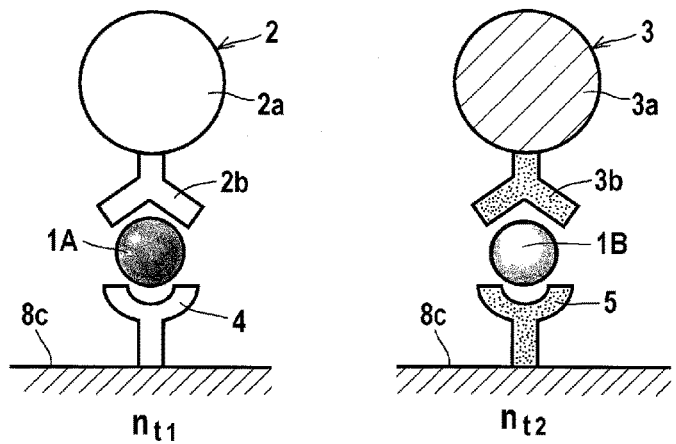
FIG. 3 is a schematic diagram illustrating ways to capture reagent particles in a preferred embodiment of the present invention.

The immunochromatography of the present invention is characterized by detecting fluorescence and light absorption at once with a specific detection device (hereinafter also referred to as a "hybrid detection device"). Hereinafter, this characteristic will be described in detail based on preferred embodiments.

[Test Piece]

First, the basic structure of a test piece that can be used in a preferred embodiment of the present invention will be described. In the test piece (test strip) for immunochromatography that can be used in the present embodiment, the following members are connected to each other in series so as to cause a capillary phenomenon.

Member for sample addition (Sample pad) 8a

Member obtained by impregnation with fluorescent silica particles (fluorescent labeling unit) 2 and gold colloid particles (light absorbing labeling unit) 3 and drying them (Conjugate pad) 8b

Membrane having test areas and a reference area (Antibody immobilizing membrane) 8c

Absorption pad 8d

In this embodiment, the members used to form the test piece may be of any type as long as they contain a membrane. Alternatively, the members listed above may be partially omitted, or other members may be used in combination with them. Besides the above members, for example, a transparent film for covering the surface may be used, or a functional sheet may be provided between the respective members. Moreover, the conjugate pad may be omitted in a method of dropping, on the sample pad, a mixed liquid of a liquid sample and labeling reagent nanoparticles.

According to this embodiment, the above-described planar test piece 10 is sandwiched between an upper casing part 6a and a lower casing part 6b to form a long test piece 100 as illustrated in FIG. 1 and FIGS. 2(a) and 2(b). On the upper casing part 6a, a detection opening 61 and an opening 62 for introducing an analyte are provided. Through the detection opening 61, irradiation light is supplied to the membrane 10 present inside, and the intensity of reflected light emitted therefrom can be detected and measured. Meanwhile, by supplying analyte liquid S to the membrane 10 through the opening 62 for introducing an analyte, measurement test can be carried out. In this description, fluorescence emitted from fluorescent particles, light resulting from absorption by light absorbing particles, and reflected light from the area other than the test areas (non-test area) upon the application of light are generically called "reflected light". Therefore, the intensity of the fluorescence from the test area $n_{t1}$ where the fluorescent particles are captured is called "the intensity ($I_2$) of reflected light from the test area $n_{t1}$", the intensity of the light absorption of the test area $n_{t2}$ where the light absorbing particles are captured is called "the intensity ($I_2$) of reflected light from the test area $n_{t2}$", and the intensity of the reflected light from the non-test area is called "the intensity ($I_c$) of reflected light from the non-test area".

In this embodiment, the membrane 8c has two test areas (first test area $n_{t1}$ and second test area $n_{t2}$) at the center of the test piece 10. A biomolecule 4 capable of capturing a target substance (a substance to be detected) 1A is placed and immobilized in the first test area $n_{t1}$. In other words, the first test area is configured to capture the fluorescent particles-containing labeling unit 2. On the other hand, a biomolecule 5 capable of capturing another target substance (another substance to be detected) 1B is placed in the second test area, at which the light absorbing labeling unit 3 is to be captured. This arrangement enables two target substances (the target substance A (1A) and the target substance B (1B)) to be distinguished and detected. Specifically, when the liquid sample s is applied, the target substances 1 (the target substance A (1A) and the target substance B (1B)) contained therein flow together with the fluorescent labeling unit 2 and the light absorbing labeling unit 3 along the flow direction L in the membrane. The fluorescent labeling unit 2 capturing the target substance A (1A) is captured in the first test area $n_{t1}$, at which the presence of it becomes ready to be identified. The target substance B (1B), which further flows along the flow direction L, is captured by the light absorbing labeling unit 3, which is captured in the second test area $n_{t2}$ so that the presence of it becomes ready to be detected.

The capture modes are summarized as follows. In this embodiment, when a sample suspected of containing the target substance A and the target substance B is used, the presence of the target substance A is determined by the fact that the intensity ($I_1$) of reflected light from the test area $n_{t1}$ where the fluorescent particles are captured is higher than the intensity ($I_c$) of reflected light from the non-test area $n_c$ (see FIG. 2) other than the test areas $n_{t1}$ and $n_{t2}$ ($I_1 > I_c$). The presence of the target substance B is determined by the fact that the intensity ($I_2$) of reflected light from the test area $n_{t2}$ where the light absorbing particles are captured is lower than the intensity ($I_c$) of reflected light from the non-test area $n_c$ ($I_2 < I_c$). The absence of both substances is determined by the fact that the intensity ($I_1$) of reflected light from the test area $n_{t1}$ where the fluorescent particles are captured, the intensity ($I_2$) of reflected light from the test area $n_{t2}$ where the light absorbing particles are captured, and the intensity ($I_c$) of reflected light from the non-test area are at substantially the same level. The presence of both substances is determined by the fact that the intensity ($I_1$) of reflected light from the test area $n_{t1}$ where the fluorescent particles are captured is higher than the intensity ($I_c$) of reflected light from the non-test area, and the fact that the intensity ($I_2$) of reflected light from the test area $n_{t2}$ where the light absorbing particles are captured is lower than the intensity ($I_c$) of reflected light from the non-test area. Therefore, the detection and measurement of a sample suspected of containing two target substances can be performed by single scanning. The term "at substantially the same level" means that optionally on the basis of the intensity ($I_c$) (a.u.) of reflected light from the non-test area, the reflected light intensities are within $\{I_c \pm (10\% \text{ of } I_c)\}$, more preferably within $\{I_c \pm (5\% \text{ of } I_c)\}$. The intensity of reflected light, although inherently varying with the measurement device or conditions, can be generalized when expressed as a relative value (ratio) for evaluation as described above. Unless otherwise stated, the strict measurement conditions are defined according to the measurement conditions described in EXAMPLES below.

The test strip for immunochromatography is described in view of FIGS. 2(a) and 2(b). However, the present invention is not limited to these descriptions. Further, a backing sheet 8e is illustrated in FIGS. 2(a) and 2(b) without omitting it. FIG. 2(a) illustrates a plan view of a preferred embodiment of the test strip (test piece) 10 for immunochromatography that can be used in the present invention, and FIG. 2(b) is an expanded longitudinal cross-sectional view of the test strip for immunochromatography illustrated in FIG. 2(a). The test strip 10 for immunochromatography according to this embodiment is provided with the sample pad 8a, the conjugate pad 8b, the membrane 8c, and the absorption pad 8d as described above. Further, each constitutional member is lined with the backing sheet 8e that is added with adhesives.

FIGS. 1 and 2 illustrate an example where the first test area $n_{t1}$, the second test area $n_{t2}$, and the reference area $n_r$ are arranged in this order. In this embodiment, the non-test area $n_c$ is defined as a part of the surface of the membrane 8c other than the first test area $n_{t1}$, the second test area $n_{t2}$, and the reference area $n_r$. It will be understood, however, that such a configuration is not intended to limit the present invention, and alternatively, for example, the order of the test areas may be reversed or the reference area may be located at any other site. The reference area $n_r$ may also be omitted.

The distance d (FIG. 2) between the first test area $n_{t1}$ and the second test area $n_{t2}$ is not limited. However, it is preferably from 2 mm to 8 mm, more preferably from 3 mm to 5 mm, in order to prevent fluorescence and light absorption from overlapping and causing the light intensities to cancel out each other.

[Target Substance]

In the present invention, the target substance 1 of the subject of detection and quantification includes antigens, antibodies, DNAs, RNAs, sugars, polysaccharides, ligands, receptors, peptides, chemical substances and the like. In the present invention, a sample containing the target substance 1 is no particularly limited, but examples of the sample includes urine, blood, and so on. An important feature of the present invention is that the target substance detected by fluorescence (target substance 1A) and the target substance detected by light absorption (target substance 1B) are different from each other. In this regard, the basic idea of the present invention differs from the technique disclosed in Patent Literature 3 in which the same target substance is detected by both fluorescence and light absorption.

The immunochromatography of the present invention allows the detection of two or more different target substances, the target substance A and the target substance B. It will be understood that the test may also be performed to determine the absence (negative) of the target substance A or B. Therefore, the liquid sample may contain the target substances A and B, only any one of the target substances A and B, or neither the target substance A nor B.

[Sample Pad]

The sample pad 8a is a constitutional member to which a sample containing a target substance is loaded. The material and the size of the sample pad are not specifically limited. Those commonly used for a product of the same type can be used.

[Conjugate Pad]

The conjugate pad 8b is a constitutional member impregnated with a fluorescent labeling unit 2 such as fluorescent silica particles and a light absorbing labeling unit 3 such as gold colloid particles, in which a target substance included in a sample, which migrates from the sample pad 8a based on capillary phenomenon, is captured and labeled by the fluorescent silica particles (labeling unit) as a result of a specific molecular recognition reaction such as antigen and antibody reaction. The content of the fluorescent labeling unit per unit area (cm$^2$) of the conjugate pad 8b is, although not particularly limited, preferably from 1 µg to 100 µg. The content of the light absorbing labeling unit is also preferably from 1 µg to 100 µg. Examples of the impregnation method include a method of coating, applying or spraying dispersion of the labeling unit, and then drying.

[Membrane]

In an antibody immobilizing part in the membrane 8c for immobilizing the antibody, test lines (first test area $n_{t1}$ and second test area $n_{t2}$) to determine presence or absence of a target substance, i.e., to determine a positive response or a negative response, are provided. These test lines $n_{t1}$ and $n_{t2}$ have target substance-capturing antibodies (test use capturing substances) 4 and 5 immobilized thereon, respectively. Further, the membrane 8c has a control line (reference area) $n_r$ immobilized with an antibody (reference use capturing substance) 7 for capturing the fluorescent silica nanoparticles. In the test areas $n_{t1}$ and $n_{t2}$, for example, the above combination causes a reaction to form a sandwich-type immunocomplex composed of immobilized antibody (test use capturing substance)-target substance-labeling unit (see FIG. 3). The shape of the determination parts (the test areas and the reference area) in the membrane are not particularly limited as long as an immobilized antibody is locally immobilized, and examples thereof include a line shape, a circular shape, a band shape, or the like. Among these, the line shape is preferable, and the line shape with width of from 0.5 to 1.5 mm is more preferable.

According to a reaction of forming the sandwich type immunocomplex, the labeled target substance is captured. Depending on level of labeling, determination of presence or absence of a target substance, i.e., determination of a positive response or a negative response, can be made. In this process, the fluorescent labeling unit such as fluorescent silica particles and the light absorbing labeling unit such as gold colloid particles are concentrated in the test areas, respectively. The concentrated part and its vicinity cause fluorescence emission, and light absorption and coloration, which can be detected and identified using a detector.

Table 1 shows typical examples of the combination of the types of the target substance, the capturing substance, the particles, and so on for the immunochromatography of the present invention. It will be understood that these examples should not be construed as limiting the present invention. In the table, each parenthesized number corresponds to each reference sign in the drawings (especially see FIG. 3).

In the present invention, such a combination of reagent components are used so that a plurality of target substances can be detected by fluorescence and light absorption in the same wavelength region, which makes it possible to detect the presence or absence and amount of target substances with high sensitivity even using a single detection unit (optical receiver). This produces the advantageous effect that the structure of the device, the measurement operation, and so on can be simplified.

It is preferable that the determination part of the antibody immobilizing membrane be formed such that it is somewhat distant from the connection end to the conjugate pad and the connection end to the absorption pad (for example, in the middle of the membrane or so). By this constitution, the reaction of forming sandwich type immunocomplex can be sufficiently completed. Further, an influence of label such as a colored or fluorescent substance in a liquid sample on measurement and an influence of a labeling unit not bound to the target substance on measurement can be preferably avoided.

Although the antibody immobilization amount in each of the antibody immobilizing parts (test areas) $n_{t1}$ and $n_{t2}$ is not particularly limited, when it has a line shape, it is preferably from 0.5 µg to 5 µg per unit length (cm). Examples of the immobilization method include a method of coating, applying or spraying an antibody solution, drying it, and immobilizing the antibody by physical adsorption. To avoid an influence of non-specific adsorption on measurement after antibody immobilization described above, the entire antibody immobilizing membrane is preferably subjected to

TABLE 1

| | | | Fluorescent side | | |
|---|---|---|---|---|---|
| No. | Target substance (1A) | Particles (2a) | Fluorescent pigment | Fluorescent wavelength Peak | Binding substance (2b) | Test use capturing substance (4) |
| 1 | Nucleoprotein of influenza A | Fluorescent silica particles | Rhodamine 6G | 555 nm | Anti-mouse antibody to nucleoprotein of influenza A | Anti-mouse antibody to nucleoprotein of influenza A |
| 2 | Nucleoprotein of influenza A | Fluorescent silica particles | Rhodamine 6G | 555 nm | Anti-mouse antibody to nucleoprotein of influenza A | Anti-mouse antibody to nucleoprotein of influenza A |
| 3 | Norovirus G I | Fluorescent silica particles | ATTO 532 | 553 nm | Anti-monoclonal antibody to norovirus GI | Anti-monoclonal antibody to norovirus GI |
| 4 | Norovirus G I | Fluorescent latex particles | Envy Green | 565 nm | Anti-monoclonal antibody to norovirus GI | Anti-monoclonal antibody to norovirus GI |

| | | | Light absorbing side | | |
|---|---|---|---|---|---|
| No. | Target substance (1B) | Particles (3a) | Light absorbing pigment | Wavelength Peak | Binding substance (3b) | Test use capturing substance (5) |
| 1 | Nucleoprotein of influenza B | Gold nanoparticles | | 528 nm | Anti-mouse antibody to nucleoprotein of influenza B | Anti-mouse antibody to nucleoprotein of influenza B |
| 2 | Nucleoprotein of influenza B | Light absorbing silica particles | Rhodamine 6G | 532 nm | Anti-mouse antibody to nucleoprotein of influenza B | Anti-mouse antibody to nucleoprotein of influenza B |
| 3 | Norovirus G II | Light absorbing silica particles | TAMRA | 546 nm | Anti-monoclonal antibody to norovirus GII | Anti-monoclonal antibody to norovirus GII |
| 4 | Norovirus G II | Colored latex particles | TAMRA | 546 nm | Anti-monoclonal antibody to norovirus GII | Anti-monoclonal antibody to norovirus GII | so-called blocking treatment in advance. For example, a method of impregnating in a buffer solution containing blocking agent such as albumin, casein, and polyvinyl alcohol for an appropriate time followed by drying can be mentioned. Examples of a commercially available blocking agent include skim milk (manufactured by DIFCO) and 4% Block Ace (manufactured by Meiji Dairies Corporation).

As described above, the membrane 8c also contains a reference area $n_r$, in which the labeling unit not captured in the test area is captured. Accordingly, presence or absence, or amount against the target substance can be determined compared to fluorescence from the test area. To perform this function, the reference use capturing substance 7 is selected so as to have the ability to bind to the test use binding substance 2b or 3b. Alternatively, two reference areas may be provided. In this case, one of the reference use capturing substances is selected so as to have the ability to bind to the test use binding substance 2b, and the other reference use capturing substance is selected so as to have the ability to bind to the test use binding substance 3b.

[Absorption Pad]

The absorption pad 8d is a constitutional membrane for absorbing a mixture of target substances 1A and 1B each of which migrates along the membrane based on capillary phenomenon and also the labeling units 2 and 3, and generating a constant flow of them at all times in the system.

The material of each of the aforementioned constitutional members is not particularly limited. Instead, members used for a test strip for immunochromatography can be used. Preferred examples of the sample pad and the conjugated pad include a pad of glass fiber such as Glass Fiber Conjugate Pad (trade name, manufactured by MILLIPORE). Preferred examples of the membrane include a nitrocellulose membrane such as Hi-Flow Plus120 (trade name, manufactured by MILLIPORE). Preferred examples of the absorption pad include a cellulose membrane such as Cellulose Fiber Sample Pad (trade name, manufactured by MILLIPORE). Examples of the backing sheet added with adhesives include AR9020 (trade name, manufactured by Adhesives Research).

[Meaning of Technical Expressions]

For clarification of the technical expressions used in this specification, the target substance 1 (1A, 1B) (although the reference numerals and symbols are denoted in FIG. 1, the present invention is not construed as being limited thereto) is a substance as an object for detection by lateral flowmetry, and it has the same meaning as the test substance in an analyte. Each of the binding substances 2b and 3b indicates a substance having binding property to the target substance and the capturing substance, respectively, and it is preferably a biomolecule. The labeling particles 2a and 3a introduced with labeling substances 2b or 3b are referred to as the labeling units 2 and 3. However, in broad sense, the term "labeling particles" may be also used to have a meaning including a labeling unit. Meanwhile, those immobilized to the membrane in the test area and capturing the labeling units 2 and 3 by way of the target substance 1 (1A, 1B) are the test use capturing substances 4 and 5. Meanwhile, that immobilized to the membrane in reference area is the reference use capturing substance 7, and the labeling units 2 and 3 are bound thereto without being mediated by the target substance 1 (1A, 1B).

[Fluorescent Labeling Unit]

As for the fluorescent labeling unit 2, fluorescent silica particles, fluorescent latex particles, and semi-conductor nanoparticles may be used in combination. In the present invention, it is particularly preferable to use the fluorescent silica particles.

As mentioned below, silica has a refractive index of from about 1.40 to about 1.46, while latex particles have a refractive index of about 1.6. Therefore, silica is a material having a light transmittance higher than that of latex. Light from the light source can efficiently enter and pass through the inside of silica. In the case of fluorescent particles, light can efficiently excite the dye in the silica particles. In the case of light absorbing particles, the dye in the silica particles can efficiently absorb light. Therefore, silica can produce more advantageous effects.

Method for producing the fluorescent silica particles is not particularly limited, and silica particles obtained by any arbitrary production method can be used. Examples of the method include a sol-gel method described in Journal of Colloid and Interface Science, 159, 150-157 (1993).

In the present invention, it is particularly preferable to use silica particles containing functional compounds, which are obtained by a method of producing colloid silica particles containing fluorescent pigment compounds as described in WO 2007/074722 A1. Specific examples of the functional compounds include a fluorescent pigment compound, a light absorbing compound, a magnetic compound, a radioactive-labeled compound, and a pH sensitive pigment compound.

Specifically, the silica particles containing functional compounds can be prepared by reacting the functional compounds with a silane coupling agent and performing polycondensation of a product obtained through a covalent bond, ionic bond, or other chemical bonds or by adsorption with one or more of silane compounds to form a siloxane bond. Accordingly, the silica particles consisting of the organosiloxane component and siloxane component that are bound to each other via siloxane bond are obtained.

As a preferred mode of producing the silica particles containing the functional compound, production can be made by reacting the functional compound having or provided with an active group such as an N-hydroxysuccinimide (NHS) ester group, a maleimide group, an isocyanate group, an isothiocyanate group, an aldehyde group, a para-nitrophenyl group, a diethoxy methyl group, an epoxy group, and a cyano group with a silane coupling agent having a substituent which reacts with those active groups (e.g., an amino group, a hydroxy group, and a thiol group), and condensing and polymerizing the product obtained by forming a siloxane bond after forming a covalent bond with one or more types of silane compounds.

The following example relates to a case in which γ-aminopropyltriethoxysilane (APS) and tetraethoxy silane (TEOS) are used as a silane coupling agent and a silane compound, respectively.

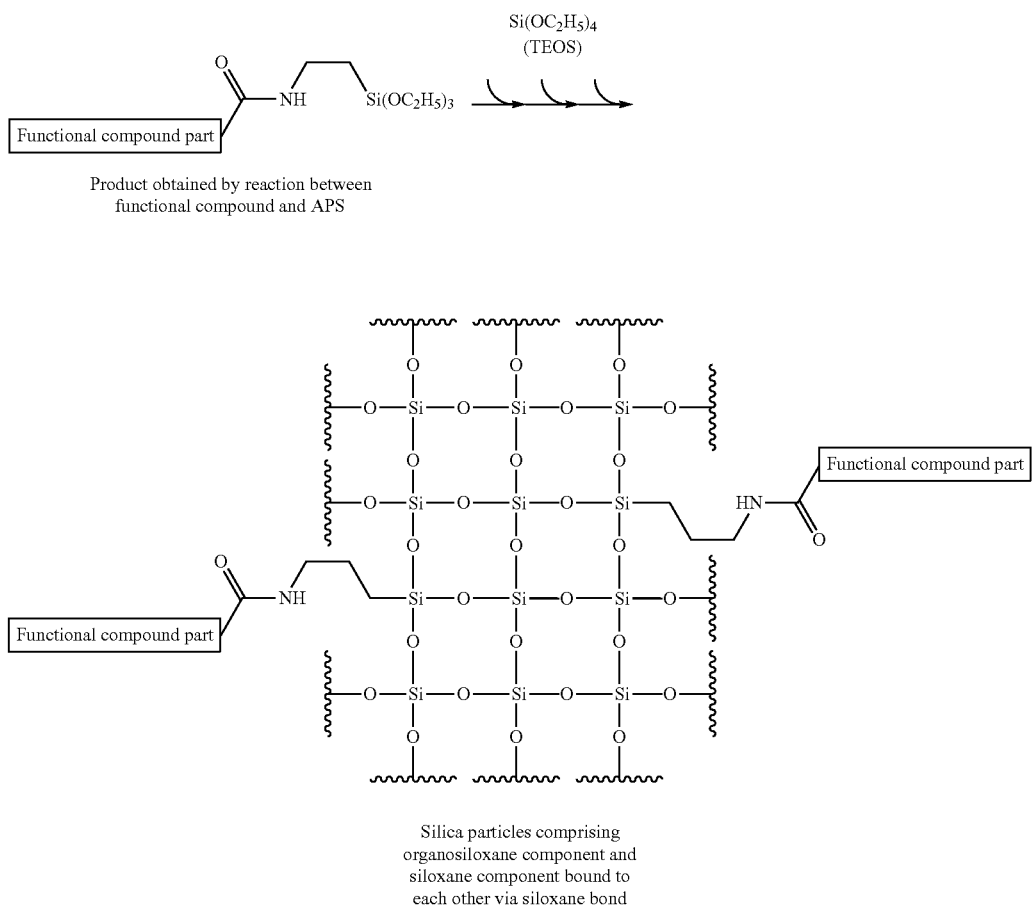

Product obtained by reaction between functional compound and APS

Silica particles comprising organosiloxane component and siloxane component bound to each other via siloxane bond Specific examples of the functional compound having or provided with an active group may include NHS ester group-containing fluorescence dye substances such as 5-(and -6)-carboxytetramethylrhodamine-NHS ester (trade name, manufactured by emp Biotech GmbH), DY550-NHS ester or DY630-NHS ester represented as follows (each trade name, manufactured by Dyomics GmbH).

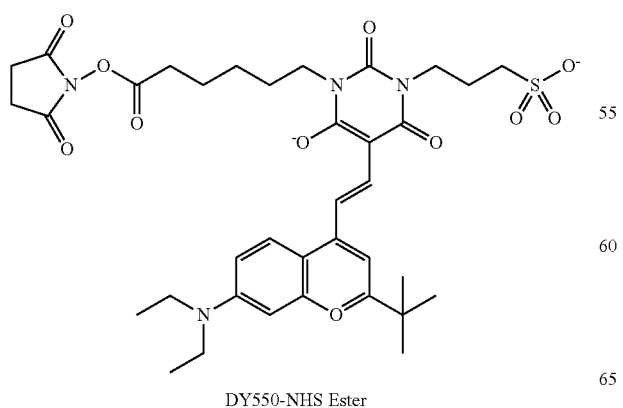

DY550-NHS Ester

-continued

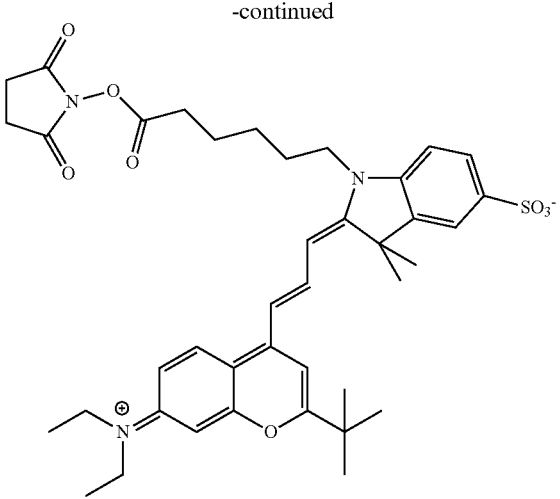

DY630-NHS Ester

Examples of the substituent-containing silane-coupling agent include an amino group-containing silane-coupling agent such as γ-aminopropyltriethoxysilane (APS), 3-[2-(2-aminoethylamino)ethylamino]-propyltriethoxysilane, N-2-(aminoethyl)-3-aminopropylmethyldimethoxysilane, and 3-aminopropyltrimethoxysilane. Among them, APS is preferable.

The silane compound to be condensed and polymerized is not particularly limited, and examples thereof include TEOS, γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyltriethoxysilane. Among them, TEOS is preferable from the point of view of forming a siloxane component to be contained in the silica particle, and besides MPS, and APS are preferable from the point of view of forming an organosiloxane component to be contained in the silica particle.

According to the production as described above, spherical or almost spherical silica particles can be prepared. Herein, "almost spherical particles" mean particles having a (major axis)/(minor axis) ratio of 2 or less.

For obtaining silica particles having a desirable average particle diameter, it is possible to remove particles having an excessively large particle diameter or an excessively small particle diameter by ultrafiltration by using an ultrafiltration membrane such as YM-10 or YM-100 (each trade name, manufactured by Millipore Corporation) or by recovering only a supernatant or precipitates after performing centrifugal separation with suitable acceleration of gravity.

As a biomolecules to be combined or absorbed on the surface of silica particles, there includes antigens, antibodies, DNAs, RNAs, sugars, polysaccharides, ligands, receptors, proteins, peptides and the like. Here, the term "ligand" means a substance capable of specifically binding to a protein, and examples thereof include substrates capable of binding to enzyme, coenzymes, regulatory factors, hormones, neurotransmitters, and the like. Thus, the ligands include low-molecular weight molecules or ions as well as polymer substances.

The average particle diameter of the fluorescent silica particles is preferably from 1 nm to 1 μm, more preferably from 20 nm to 500 nm, and particularly preferably from 200 nm to 400 nm.

In the present invention, the average particle diameter is an average diameter of the circle (average circle-equivalent diameter) obtained by measuring the total projected area of 100 pieces of randomly-selected labeling reagent silica particles for example in an image obtained under transmission electron microscope (TEM) or scanning electron microscope (SEM) using an image processing equipment, dividing the total area with the number of the labeling reagent silica particles (100 pieces), and determining the circle having an area equivalent to that.

Further, the "average particle diameter" indicates an average particle diameter of particles consisting of only primary particles, which is different from the "particle size according to a dynamic light scattering method" described below having a concept including secondary particles formed by aggregation of primary particles.

The density of the latex particles is as small as 1 g/cm³. If the size of the latex particles is reduced, therefore, it can be impossible to separate them by centrifugation, so that they cannot be used as labeling particles in some cases. In contrast, silica has a relatively high density (e.g., about 2 g/cm³). Even if the size of silica particles is reduced, they can be easily separated by centrifugation and advantageously used as labeling particles. Therefore, silica particles with a size smaller than that of the latex particles can be used in the detection according to the present invention, which makes it possible to select the size of the particles to be used from a wider range and to select particles with a size small enough to optimize the characteristics of migration in the membrane. From these points of view, it is preferable to use the silica particles in the present invention.

Silica particles have a low refractive index as mentioned below, so that they will not cause light scattering when influenced by water around them, which is also the advantage of the use of the silica particles. In particular, the present invention is also intended to improve the accuracy of the detection of an analyte in a very small amount such as 10 ng/mL, as shown in Examples below. Also from this point of view, the silica particles are preferably used to form labeling reagents.

<Refractive Index>589 nm, 23° C.

| | |
|---|---|
| Polystyrene beads | 1.59 |
| Silica particles | from 1.40 to 1.46 |
| Water | 1.33 |

(Chronological Scientific Tables edited by National Astronomical Observatory of Japan)

$$\text{Intensity of reflected light } R=(n_0-n_i)^2$$

$n_0$: Refractive index of water
$n_i$: Refractive index of particles
R (Polystyrene beads)=$7.93\times10^{-3}$
R (Silica particles)=from $6.57\times10^{-4}$ to $2.17\times10^{-3}$ As described herein, the "particle size according to the dynamic light scattering method" is measured by the dynamic light scattering method, and it is a concept including secondary particles formed by aggregation of primary particles as well as primary particles, different from average particle diameter. This particle size is an indicator for evaluating dispersion stability of complex particles described above.

Examples of a device for measuring the particle size according to the dynamic light scattering method include Zetasizer Nano (trade name, manufactured by Malvern Instruments Ltd.). According to the method, fluctuation in light scattering intensity over time that is caused by light scatterers such as fine particles is measured, the speed of the light scatterers in Brownian motion is calculated based on an autocorrelation function, and the particle size distribution of the light scatterers is determined based on the results.

The particles to be used in the present invention preferably have monodispersion as a granular substance. The variation coefficient, so-called CV value, of the particle size distribution is not specifically limited, but preferably 10% or less, and more preferably 8% or less.

[Light Absorbing Labeling Unit]

As in the case of the fluorescent labeling unit 2, the light absorbing labeling unit 3 is preferably such that the surface of the light absorbing fine particles 3a is modified with a biomolecule (binding substance) 3b or the like having a high ability to bind to the target substance and the reference use capturing substance. The surface of the light absorbing fine particles can be modified in the same manner as in the case of the fluorescent fine particles.

The kind and shape of the light absorbing fine particulates are not specifically limited. Preferred examples of the average particle diameter, constitutional materials, or the like of the light absorbing fine particulates are the same as those of the fluorescent fine particulates described above. The labeling substance is not particularly used as long as the constitutional material of the fine particulates has a light absorbing property. When a labeling substance (light absorbing substance) is applied, examples thereof that may be used include an organic pigment such as a polycyclic pigment and an azo pigment, and an inorganic pigment such as carbon black and ultramarine blue. For example, the light absorbing substance may be incorporated in the silica particles or latex particles. Further, the following semi-conductor particulates may be also preferably used as light absorbing fine particulates.

Semi-conductor Particles or the Like

Materials of the semi-conductor particles are not specifically limited, but preferred examples thereof include ZnO, ZnS, ZnSe, ZnTe, CdO, CdS, CdSe, CdTe, HgS, HgSe, HgTe, InP, InAs, GaN, GaP, GaAs, $TiO_2$, $WO_3$, PbS, and PbSe. For example, semi-conductor nanoparticles described in Japanese Patent No. 3897285 or the like may be used. The surface of the semi-conductor nanoparticles may be modified by substituting an atom such as S, O, Se, Te, P, As, and N present on surface of semi-conductor nanoparticles with a —SH group of a thiol compound. Examples of the gold particles and the metal nanoparticles that may be used include colloidal gold particles and colloidal metal particles described in JP-A-2003-26638 or the like. Specific examples of the colloidal metal particle include colloidal metal particles of platinum, copper, iron oxide or the like. Examples of the inorganic crystals include iron oxide (III) ($Fe_2O_3$), silver oxide (I) ($Ag_2O$), tin oxide (IV) ($SnO_2$), titanium oxide (IV) ($TiO_2$), and indium tin oxide (ITO). The inorganic crystals described in JP-A-2005-76064 may be used, for example.

The colloidal gold particles generally have a high surface plasmon effect and can efficiently absorb visible light wavelengths so that the visibility of the particles is high. Further, the colloidal gold particles have a peak absorption wavelength almost equal to that of a green laser. Therefore, when the colloidal gold particles used in combination with fluorescent particles capable of being excited with a green laser (such as silica particles containing rhodamine 6G), it is possible to build a measurement device for detecting fluorescence and light absorption at once with high fluorescence detection sensitivity and high light-absorption detection sensitivity.

Light Absorption Coefficient

The light absorbing fine particulates preferably absorb visible light and exhibit a color which is visually recognizable. Further, they are the particles preferably having molar absorption coefficient ε of $5 \times 10^6$ $M^{-1} cm^{-1}$ or higher. Those having the molar absorption coefficient ε of from $5 \times 10^7$ $M^{-1} cm^{-1}$ to $1 \times 10^{10}$ $M^{-1} cm^{-1}$ are more preferable.

As described herein, the molar absorption coefficient ε can be calculated based on the following Lambert-Beer equation.

$$A = \mathrm{Log}_{10}(I_0/I) = \varepsilon bp = a_s bp'$$

A: Absorbance
Intensity of transmitted light
$I_0$: Intensity of incident light
ε: Molar absorption coefficient ($M^{-1} cm^{-1}$)
b: Light passage length (cm)
p: Concentration of labeling particles (including mixture dispersion of coloration particles and fluorescent particulates) (M (mol/L))
$a_s$: Relative absorption coefficient
p': Concentration of labeling particles (including mixture dispersion of coloration particles and fluorescent particulates) (g/L)}.

The concentration p' (g/L) is a value obtained by recovering only the labeling particles from a constant amount (e.g., 1 mL) of dispersion containing labeling particles and determining the dried mass. Meanwhile, the concentration p (mol/L) is a value obtained by determining the size of the labeling particles from a TEM image, calculating the volume of a single particle, determining mass of a single particle in view of density of the particle (e.g., 2.3 $g/cm^3$ for silica particles), recovering only the labeling particles from a constant amount (e.g., 1 mL) of dispersion containing labeling particles, and determining the mole number in view of the dried mass of the labeling particles. In the present specification, the expression "molar absorption coefficient ε of the labeling particles" means molar absorption coefficient ε of labeling particles in the dispersion, which is obtained by measuring absorbance of dispersion containing the labeling particles and applying the result to the Lambert-Beer equation described above. The absorbance, absorption spectrum, and ε of the labeling particles can be measured from a dispersion such as aqueous dispersion, ethanol dispersion, or N,N-dimethyl formamide dispersion by using any light absorption spectrophotometer or a plate reader.

[Fluorescence Wavelength and Light Absorption Wavelength]

In a preferred embodiment of the present invention, the fluorescent particles 2a (fluorescent labeling unit 2) and the light absorbing fine particles 3a (light absorbing labeling unit 3) are preferably such that the fluorescence excitation wavelength (typically peak top) [$\lambda_1$] and the absorption wavelength (typically light absorption peak top) [$\lambda_2$] are in the same wavelength region. The "same wavelength region" may be any region as long as the desired effect of the present invention can be produced, namely, fluorescence and light absorption can be detected and read as opposite peaks with a single detection unit (optical receiver). It is preferable that in the immunochromatography production process, the labeling particles should be visually observed, in other words, colored. Therefore, the fluorescence excitation wavelength and the light absorption wavelength ($\lambda_1$ and $\lambda_2$) are preferably from 300 nm to 800 nm. In view of the availability of the fluorescent dye and the coloring dye and so on, the fluorescence detection wavelength region and the light absorption detection wavelength region ($\lambda_1$ and $\lambda_2$) are preferably from 350 to 700 nm, more preferably from 400 nm to 650 nm. In view of the light sensitivity characteristics of general-purpose detectors (photosensors), the wavelength regions are particularly preferably from 500 nm to 650 nm. As used herein, the term "peak" refers to the whole of a peak top and its vicinity, and in a narrow sense, it means a peak top (apex). In visual observation, the fluorescence in the above wavelength region appears substantially green, and the light absorption (coloration) appears substantially red. The difference ($\Delta\lambda = \lambda_1 - \lambda_2$) between the fluorescence excitation wavelength ($\lambda_1$) and the absorption wavelength ($\lambda_2$) is preferably, but not limited to, 60 nm or less, more preferably 30 nm or less, and particularly preferably 10 nm or less, in view of suitable one-time detection. Although the difference does not have any lower limit, it is practically 0.5 nm or more. In the present invention, unless otherwise specified, the wavelength of light is measured under the conditions described in EXAMPLES below (including the device, the measurement temperature, and so on). For example, when the fluorescent dye and the light absorbing dye used are both rhodamine 6G, the difference between the fluorescence excitation wavelength ($\lambda_1$) and the absorption wavelength ($\lambda_2$) is 23 nm. When ATTO532 is used as the fluorescent and TAMRA is used as the light absorbing dyes, the difference is 7 nm. These conditions satisfy the above relationship.

[Detection Method]

Figure 4:
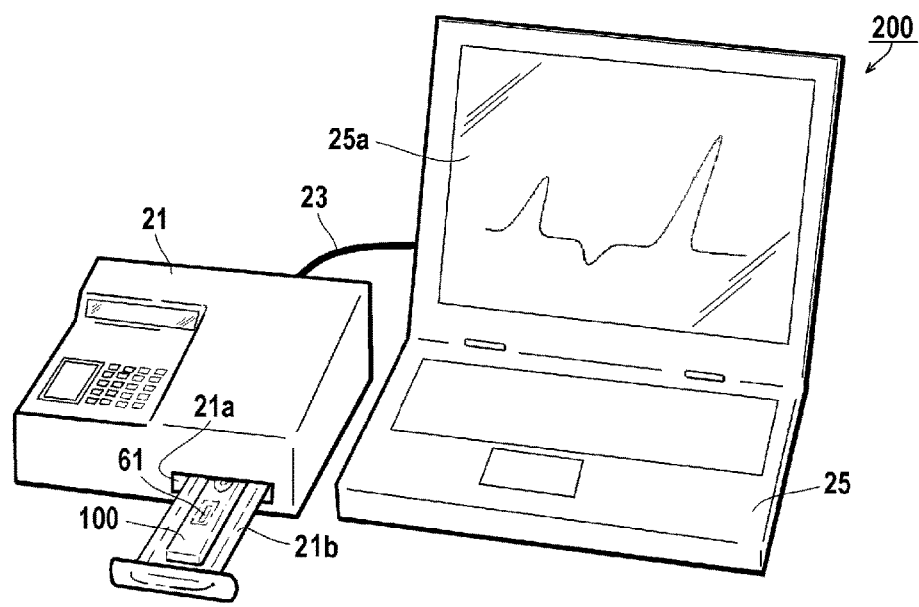
FIG. 4 is a perspective view schematically illustrating an example of a hybrid detection device according to a preferred embodiment of the present invention.

In the immunochromatography of the present invention, the test piece is used, and the fluorescence and the light absorption (coloration) produced from the test piece are detected and measured respectively at once with a hybrid detection device. FIG. 4 is a perspective view schematically illustrating a preferred embodiment of the detection device. The detection device 200 is configured to have a main detection unit 21 and a personal computer (control unit) 25, which are connected with wiring 23. A detection part 20 (see FIG. 5) is built in the main detection unit 21. The detection part 20 is configured to move at a position corresponding to the detection opening 61 of a long test stick 100, which is introduced from a sample inlet 21a along a sample guide 21b, and to scan the surface of the test piece 10 exposed from the detection opening 61. This configuration allows the detection and measurement of the fluorescence and light absorption of the test areas ($n_{f1}$ and $n_{f2}$) and the reference area $n_r$ in the test piece 10 or the intensity ($I_1$, $I_2$, $I_c$) of reflected light from each area.

Figure 5:
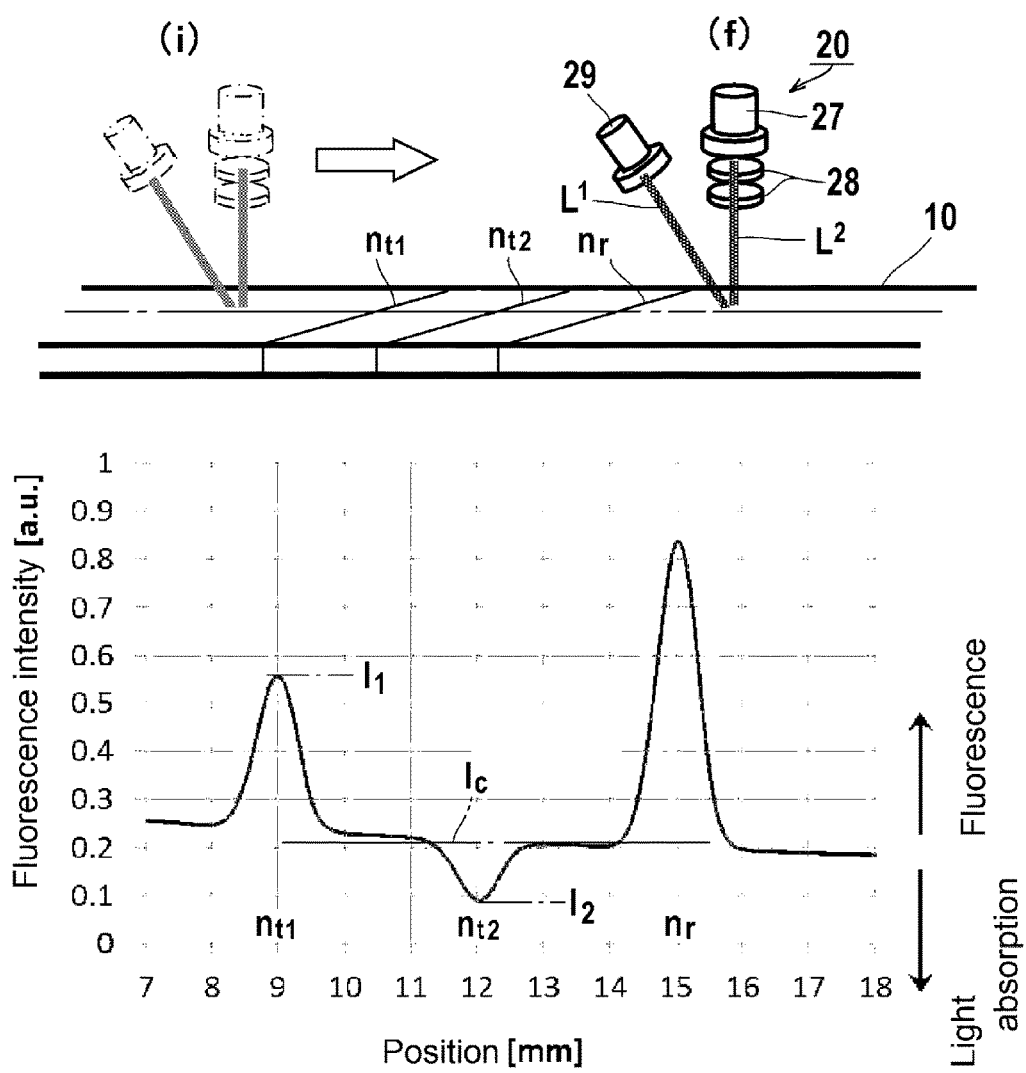
FIG. 5 is a diagram schematically illustrating the relationship between test areas of a test piece and fluorescence and light absorption peaks detected in the immunochromatography of the present invention.

The detection part 20 is composed of an optical receiver 27, receiver lenses 28, and a light irradiator 29. The upper part of FIG. 5 schematically illustrates the operation performed when the detection part 20 scans the surface from the initial position (i) to the final position (f) along the test areas ($n_{f1}$ and $n_{f2}$). The lower part of FIG. 5 illustrates an example in which fluorescence peaks and a light absorption peak are detected in the operation. As shown in FIG. 5, an upward-facing fluorescence peak is detected in the first test area $n_{f1}$, and a downward-facing light absorption peak is detected in the second test area $n_{f2}$. In this example, a fluorescence peak is detected at the reference line $n_r$. Since the test areas are apart from each other, these peaks are detected without overlapping each other, and the light intensities do not cancel each other out. In this way, both the fluorescence and the light absorption are successfully measured in once time with a single detection part (optical receiver), which is an advantage of the present invention.

In this embodiment, the control unit 25 of the hybrid detection device commands the detection part to scan the test piece and to detect and measure the fluorescence peak and the light absorption peak at once. It will be understood that this embodiment is non-limiting, and the control unit may be configured in any suitable way. For example, the control unit may be incorporated in the main detection unit 21. In this embodiment, the personal computer (detection part) 25 also serves as means for read-out and analysis. The means for read-out and analysis is adapted to identify the fluorescence peak as an upward- or downward-facing peak; to identify the light absorption peak as a peak facing downward or upward opposite to the fluorescence peak, to detect the target substances A1 and B1, respectively; and to display the results on a display unit 25a. As mentioned above, in the detection and analysis, the presence or absence or the amount of the target substances can be determined not only by the optical peak analysis but also generally from the reflected light intensities ($I_1$, $I_2$, $I_c$).

In this embodiment, the hybrid detection device 200 is preferably used as a quantitative measurement device for quantifying the target substances from the fluorescence peak area and/or the light absorption peak area. When such quantification is performed, the amount of the analyte substance is preferably determined by comparison with a calibration curve for peak area, which is prepared in advance. To know an approximate amount or understand the relative relationship between the analyte substances detected from the fluorescence peak and the light absorption peak, quantitative measurement may also be performed using an integrated intensity calculated for each peak without any calibration curve.

The present invention makes it possible to measure a plurality of analyte substances (target substances) with a single test piece, which is advantageous in that fluctuations between test pieces, errors in the preparation of samples, or a wrong operation (such as misplacement of samples) can be successfully prevented. In addition, a detection device with a simple structure can also be provided, which makes it possible to move the place where the test is performed or to perform the test at dispersed places. Such advantages will be particularly significant when the present invention is used for public health services where a large number of samples are to be tested and measured.

As described above, the method of detecting a target substance according to the immunochromatography of the present invention is preferably a method containing steps of concentrating on a determination part the migrating the labeling unit based on capillary phenomenon, and performing the determination. For example, it is preferably performed by immunochromatography or using a micro flow chip or the like. In this case, the silica particles may be preferably used as a labeling unit for lateral flowmetry. In addition, in the present invention, it is preferable to detect target substances by using lateral flow type immunochromatography.

With regard to a method for producing the test strip, a sample pad, a conjugate pad, an antibody immobilizing membrane, and an absorption pad are overlaid in that order while both ends of each member are attached to the neighboring member such that they are overlapped with each other within a range of 1 to 5 mm (preferably, on a backing sheet) so as to easily cause capillary phenomenon between the respective members.

The fluorescence/light absorption detection system for the immunochromatography preferably consists of at least (1) a test strip consisting of a sample pad, a conjugate pad, an antibody immobilizing membrane and an absorption pad, and (2) an excitation light source.

According to the fluorescence detection system, from the viewpoint of preferably detecting the fluorescence emitted from the silica particles (labeling units), it is preferable that excitation light source (light irradiator) emits excitation light with a wavelength of from 500 nm to 550 nm. Examples of the excitation light source include a mercury lamp, a halogen lamp, and a xenon lamp. Excitation light illuminated from a laser diode or light emitting diode is particularly preferably used.

Further, the fluorescence detection system is preferably equipped with a filter for selectively transmitting light of specific wavelength from the excitation light source. Further, from the viewpoint of precisely detecting the fluorescence, it is more preferably equipped with a filter which is capable of removing the excitation light and transmitting only the fluorescence.

In particular, the optical receiver is preferably a photomultiplier tube, CCD detector or CMOS detector capable of receiving the fluorescence and detecting the light absorption (coloration). Accordingly, fluorescence with visually undeterminable intensity or wavelength can be detected, and further quantification of target substances can be made as its fluorescence intensity can be measured, enabling detection and quantification with high sensitivity. Concerning the light sensitivity characteristics of the optical receiver, the optical receiver to be used preferably has high sensitivity (sensitivity peak) to light in the wavelength region of from 400 to 700 nm, more preferably in the wavelength region of from 500 to 600 nm, in view of availability of high sensitivity products.

EXAMPLES

The present invention will be described in more detail based on examples given below, but the invention is not meant to be limited by these.

Preparation Example 1 (Preparation of Fluorescent Silica Nanoparticles)

2.9 mg of 5-(and-6)-carboxyrhodamine 6G.succinimidyl ester (trade name, manufactured by EMP Biotech GmbH) was dissolved in 1 mL of dimethyl formamide (DMF). Then, 1.3 µL of APS was added thereto and the reaction was carried out for 1 hour at room temperature (25° C.).

600 µL of the resulting reaction liquid was admixed with 140 mL of ethanol, 6.5 mL of TEOS, 35 mL of distilled water, and 15.5 mL of 28% by mass ammonia water, and the reaction was allowed to occur at room temperature for 24 hours.

The reaction solution was centrifuged at a gravitational acceleration of 15,000×g for 30 minutes, and the supernatant was removed. 4 mL of distilled water was added to the precipitated silica particles for dispersion, and the dispersion was centrifuged again at a gravitational acceleration of 15,000×g for 20 minutes. Further, this washing operation was repeated twice additionally, for removal of the unreacted TEOS, ammonia and others contained in the silica nanoparticle dispersion. Thus, 1.65 g of silica nanoparticles having an average particle diameter of 227 nm were obtained. Yield ratio: about 94%

Preparation Example 2 (Preparation of Complex Particles of Fluorescent Silica Particles and an Antibody)

To 100 µL of dispersion solution (dispersion medium: distilled water) of the fluorescent silica particles (average particle diameter; 197 nm) containing rhodamine 6G at a concentration of 5 mg/mL, which had been used in Preparation Example 1, 775 µL of distilled water, 100 µL of an aqueous solution of sodium alginate with a concentration of 10 mg/mL (weight average molecular weight: 70,000), and 25 µL of an aqueous ammonia solution with a concentration of 28% by weight were added. Then, the mixture was slowly stirred for 1 hour at room temperature (24° C.). The obtained colloid was subjected to centrifugation for 30 minutes with a gravitational acceleration of 12,000×g, and then the supernatant was removed. Distilled water (875 µL) was added thereto and the particles were re-dispersed. Subsequently, 100 µL of an aqueous solution of sodium alginate with a concentration of 10 mg/mL was added thereto, and the mixture was stirred well using a stirrer followed by addition of 25 µL of an aqueous ammonia solution with a concentration of 28% by weight and slowly stirred for 1 hour. The resulting colloid was subjected to centrifugation for 30 minutes with a gravitational acceleration of 12,000×g, and then the supernatant was removed. After adding 1 mL of distilled water, particles were dispersed. Centrifugal isolation and dispersion with distilled water were repeated twice in the same manner as above for washing the particles, which were then dispersed in 200 µL of distilled water to obtain colloid of complex particles of the silica particles containing rhodamine 6G/aliginic acid (yield: 2.5 mg/mL× 200 µL).

To the colloid of complex particles of the fluorescent silica particles containing rhodamine 6G/aliginic acid, 100 µL of 0.5 M 2-morpholinoethanesulfonic acid buffer (pH 6.0), 395 µL of distilled water, 230 µL of an aqueous solution of 50 mg/mL NHS (N-hydroxysuccinimide), and 75 µL of 19.2 mg/mL aqueous solution of EDC (1-ethyl-3-(3-dimethylaminopropyl)carbodiimide) were added in order followed by mixing for 10 min.

The colloid was subjected to centrifugation for 10 minutes with a gravitational acceleration of 12,000×G, and the supernatant was removed. Then, 400 µL of 50 mM $KH_2PO_4$ (pH 7.0) was added for dispersing the particles. Further, 100 µL (0.5 mg/mL) of an anti-goat antibody to nucleoprotein of influenza A (Anti-Influenza A Virus Nucleoprotein, antibody, Goat-Poly, manufactured by LifeSpan Biosciences) was also added, and by slow mixing at room temperature for 30 min. Thus, the silica nanoparticles were linked with the antibody via covalent bond.

Subsequently, the colloid was subjected to centrifugation for 10 minutes with a gravitational acceleration of 12,000× G, and the supernatant was removed. Then, 1 mL of 50 mM $KH_2PO_4$ (pH 7.0) was added for dispersing the particles. After the centrifugation for 10 minutes with a gravitational acceleration of 12,000×G, the supernatant was removed. Then, 1 mL of 50 mM $KH_2PO_4$ (pH 7.0) was added for dispersing the particles. After the centrifugation for 10 minutes with a gravitational acceleration of 12,000×G, the supernatant was removed. Further, 1 mL of 50 mM $KH_2PO_4$ (pH 7.0) was added for dispersing the particles, and then 1 mL of colloid of complex particles of the silica particles and the antibody to nucleoprotein of influenza A with a concentration of 0.5 mg/mL was obtained.

Preparation Example 3 (Preparation of Complex Particles of Gold Colloid Particles and an Antibody)

To 0.5 mL of gold colloid (particle diameter: 40 nm), 100 µL of 50 µg/mL antibody to nucleoprotein of influenza B (Anti-Human Influenza B, Monoclonal (Clone 9D6), manufactured by Takara Bio Inc.) was added, and then the mixture was allowed to stand at room temperature for 10 minutes. Subsequently, 100 µL of a phosphate buffer (pH 7.5) containing 1% by weight of bovine serum albumin was added, and the mixture was further allowed to stand at room temperature for 10 minutes. The mixture was then centrifuged at 8,000×G for 15 minutes, and the supernatant was removed. Then, 100 µL of a phosphate buffer (pH 7.5) containing 1% by weight of bovine serum albumin was added to disperse the particles.

Production Example (Detection Device)

A detection device was built, containing: a detection unit composed of a light source, an optical filter, and a photomultiplier tube (PMT); a mechanism for linearly moving the detection unit at a constant speed by means of a motor; and a recording mechanism for recording, every 50 µsec, the intensity of light received by the PMT. In the detection unit, the light source is a 532 nm laser diode. The detection unit has a mechanism configured so that light is applied from the laser diode to the sample and the resulting reflected light is allowed to pass through an optical filter capable of transmitting only light with a wavelength of 550 nm or more and then received by a photomultiplier tube (PMT) (Head-on PMT (trade name) manufactured by Hamamatsu Photonics K.K.). In this example, the reflected light was detected at room temperature (25° C.) in all cases.

Example 1 (Manufacture of the Test Strip for Immunochromatography)

The colloid of the complex particles of fluorescent silica particles and an antibody that had been obtained from Preparation Examples 1 and 2 (240 µL), the complex particles of gold colloid particles and an antibody that had been obtained from Preparation Example 3 (100 µL) and 50 mM $KH_2PO_4$ (pH 7.0, 460 µL) were admixed with each other. The resulting mixture (800 µL) was uniformly coated on Glass Fiber Conjugate Pad (GFCP, manufactured by MILLIPORE) (8×150 mm). After drying overnight at room temperature under reduced pressure in a desiccator, a conjugate pad containing the complex particles which had been obtained from Preparation Examples was manufactured.

Next, an antibody immobilizing membrane was produced as follows.

At the about 9 mm from the end of the membrane (length: 25 mm, trade name: Hi-Flow Plus120 membrane, manufactured by MILLIPORE), a solution ((50 mM $KH_2PO_4$, pH 7.0)+5% sucrose) containing an anti-mouse antibody to nucleoprotein of influenza A (Influenza A nucleoprotein, InA245, manufactured by HyTest) in an amount of 1 mg/mL was coated in a coating amount of 0.75 µL/cm to give a test line with width of about 1 mm.

Subsequently, as a test line for the influenza B with width of about 1 mm, a solution ((50 mM $KH_2PO_4$, pH 7.0)+5% sucrose) containing an anti-mouse antibody to nucleoprotein of influenza B (Influenza B Virus Nucleoprotein antibody, manufactured by Fitzgerald) in an amount of 1 mg/mL was coated in a coating amount of 0.75 µL/cm. A distance d between the test line for the influenza A and the test line for the influenza B was set to 3 mm.

Subsequently, as a control line with width of about 1 mm, a solution ((50 mM $KH_2PO_4$, pH 7.0), sugar free) containing a goat anti-mouse IgG antibody (AKP Goat anti-mouse IgG Antibody, manufactured by BioLegend) in an amount of 1 mg/mL was coated in a coating amount of 0.75 µL/cm followed by drying for 30 min at 50° C. A distance between the test line for the influenza B and the control line was set to 3 mm.

The sample pad (Glass Fiber Conjugate Pad (GFCP), manufactured by MILLIPORE), the above-described conjugate pad, the antibody immobilizing membrane, and the absorption pad (Cellulose Fiber Sample Pad (CFSP), manufactured by MILLIPORE) were assembled in this order on a backing sheet (trade name; AR9020, manufactured by Adhesives Research). The membrane was configured in such an orientation that the test line for influenza A was on the conjugate pad side, while the control line was on the absorption pad side.

Quick Determination of Nucleoproteins of Influenza

According to the composition shown in Table 2, a liquid mixture of the influenza A nucleoprotein and the influenza B nucleoprotein was prepared.

Subsequently, 100 µL of the liquid mixture was added dropwise to the sample pad part of the test strip. After 15 minutes, the measurement was performed with the detector of Production Example, and the test line for the influenza A was observed with a fluorescence reader, while the test line for the influenza B was visually observed. As described herein, the "fluorescence reader" indicates a device consisting of a laser diode with a wavelength of 532 nm and an optical filter, by which the laser diode illuminates a line area of the membrane and only the fluorescence emitted from fluorescent particles is observed by monitoring the line through the optical film.

As an example of the measurement result, FIG. 5 shows a fluorescence profile that was obtained when the membrane No. 16 was measured. In FIG. 5, the upward-facing peak at the position of about 9 mm is derived from the fluorescent silica particles binding to the test line for influenza A. The downward-facing peak at the position of about 12 mm is derived from gold colloid binding to the test line for influenza B. The upward-facing peak at the position of about 15 mm is derived from the fluorescent silica particles binding to the control line.

Table 2 shows the results of the measurement and the determination. In Table 2, "Line $n_{t1}$" represents the test line for the influenza A, and "Line $n_{t2}$" represents the test line for the influenza B. The base line value for the determination system is the fluorescence intensity value at the position of 10.5 mm on the membrane. The line $n_{t1}$ value is the peak value ($I_1$) of the fluorescence intensity of the test line for influenza A. The line $n_{t2}$ value is the peak value ($I_2$) of the fluorescence intensity of the test line for influenza B. Concerning the observation of the lines, the line $n_{t1}$ was observed with a fluorescence reader, while the line $n_{t2}$ was visually observed. In Table 2, "+" represents a visible test line, while "−" represents a non-visible test line. Herein, the "fluorescence reader" is a device configured so that light is applied from a 532 nm laser diode as a light source and the resulting reflected light is visually observed through an optical filter capable of transmitting only light with a wavelength of 540 nm or more.

Figure 6:
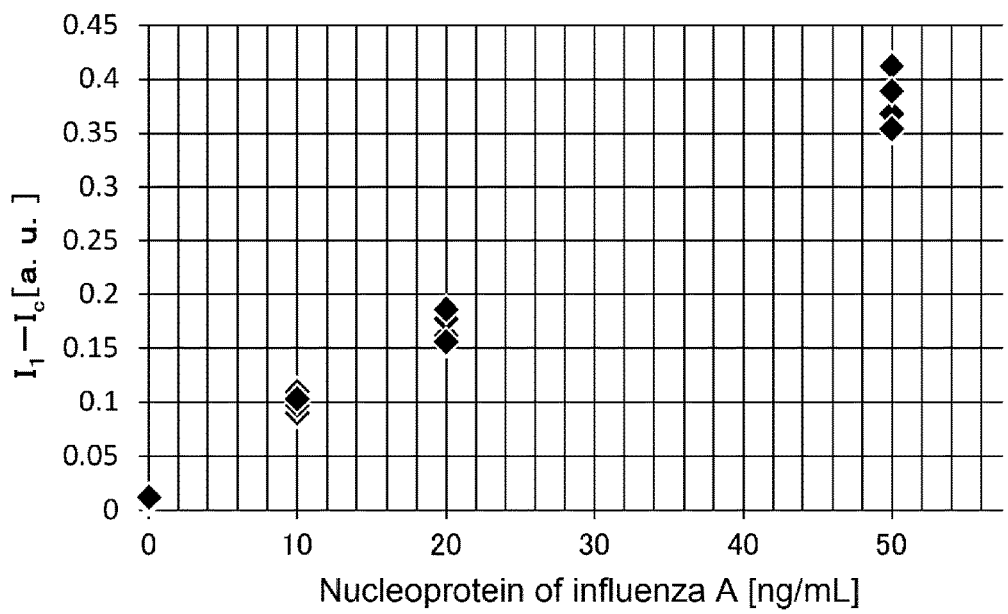
FIG. 6 is a graph illustrating the correlation between the concentration of the influenza A nucleoprotein and the $(I_1-I_c)$ value.
Figure 7:
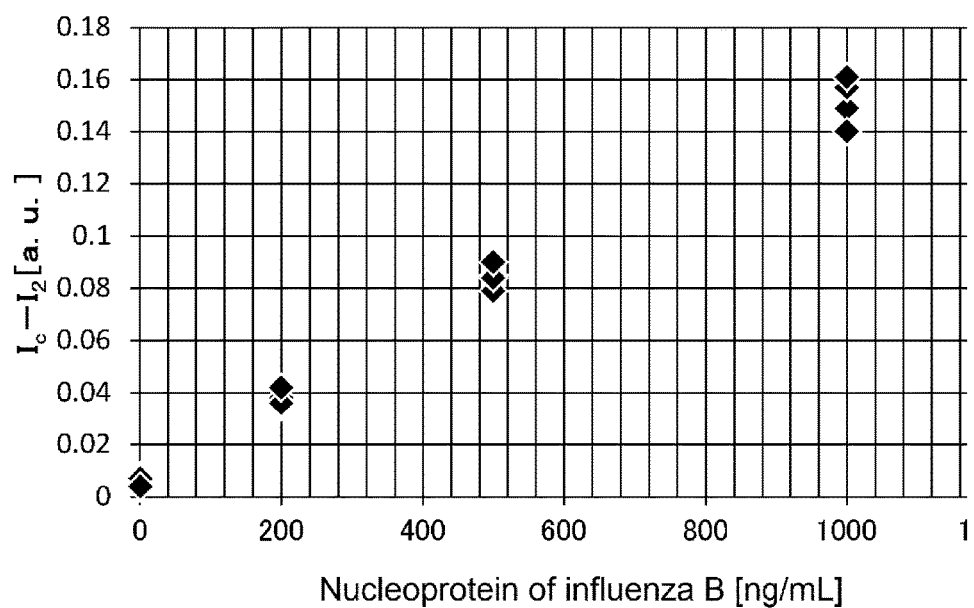
FIG. 7 is a graph illustrating the correlation between the concentration of the influenza B nucleoprotein and the $(I_c-I_2)$ value.

FIG. 6 shows the correlation between the concentration of the influenza A nucleoprotein and the ($I_1-I_c$) value. FIG. 7 shows the correlation between the concentration of the influenza B nucleoprotein and the ($I_c-I_2$) value.

The results show that on the test line for the influenza A, the difference ($I_1-I_c$) between the peak fluorescence intensity of the line and the base-line fluorescence intensity (see the auxiliary line $I_c$ in FIG. 5) for the sample containing 10 ng/mL or more of the influenza A nucleoprotein was significantly larger than the value for the sample containing no influenza A nucleoprotein. More specifically, the difference ($I_1-I_c$) between the peak fluorescence intensity of the line and the base-line fluorescence intensity for the sample containing 100 ng/mL or more of the influenza A nucleoprotein was 30% or more of the base-line fluorescence intensity $I_c$. To the contrary, the value for the sample containing no influenza A nucleoprotein was 5% or less. In the observation with the fluorescence reader, the detection limit was 20 ng/mL. It is apparent, therefore, that the present detection method has higher sensitivity.

Similarly, on the test line for the influenza B, the difference ($I_c-I_2$) between the base-line fluorescence intensity and the peak fluorescence intensity of the line for the sample containing 200 ng/mL or more of the influenza B nucleoprotein was significantly larger than the value for the sample containing no influenza B nucleoprotein. More specifically, the difference ($I_c-I_2$) between the base-line fluorescence intensity and the peak fluorescence intensity of the line for the sample containing 200 ng/mL or more of the influenza B nucleoprotein was 15% or more of the base-line fluorescence intensity $I_c$. To the contrary, the value for the sample containing no influenza B nucleoprotein was 4% or less. In the visual observation, the detection limit was 500 ng/mL. It is apparent, therefore, that the present detection method has higher sensitivity.

These results show that the present detection method allows the detection of two items at once by a single measurement and has higher sensitivity than observation with a fluorescence reader or visual observation.

TABLE 2

| No. | Liquid mixture composition A type [ng/mL] | Liquid mixture composition B type [ng/mL] | Measured values [a.u.] Base $n_c$ ($I_c$) | Measured values [a.u.] Line $n_{t1}$ ($I_1$) | Measured values [a.u.] Line $n_{t2}$ ($I_2$) | $I_1 - I_c$ | $I_c - I_2$ | Observation of lines Line $n_{t1}$ | Observation of lines Line $n_{t2}$ |
|---|---|---|---|---|---|---|---|---|---|
| 1  | 0  | 0    | 0.255 | 0.267 | 0.247 | 0.012 | 0.008 | − | − |
| 2  | 10 | 0    | 0.222 | 0.312 | 0.218 | 0.090 | 0.004 | − | − |
| 3  | 20 | 0    | 0.229 | 0.391 | 0.222 | 0.162 | 0.007 | + | − |
| 4  | 50 | 0    | 0.224 | 0.636 | 0.220 | 0.412 | 0.004 | + | − |
| 5  | 0  | 200  | 0.226 | 0.235 | 0.188 | 0.009 | 0.038 | − | − |
| 6  | 10 | 200  | 0.228 | 0.338 | 0.193 | 0.110 | 0.035 | − | − |
| 7  | 20 | 200  | 0.221 | 0.398 | 0.185 | 0.177 | 0.036 | + | − |
| 8  | 50 | 200  | 0.229 | 0.597 | 0.187 | 0.368 | 0.042 | + | − |
| 9  | 0  | 500  | 0.282 | 0.293 | 0.197 | 0.011 | 0.085 | − | + |
| 10 | 10 | 500  | 0.267 | 0.364 | 0.188 | 0.097 | 0.079 | − | + |
| 11 | 20 | 500  | 0.273 | 0.459 | 0.189 | 0.186 | 0.084 | + | + |
| 12 | 50 | 500  | 0.281 | 0.670 | 0.191 | 0.389 | 0.090 | + | + |
| 13 | 0  | 1000 | 0.257 | 0.269 | 0.108 | 0.012 | 0.149 | − | + |
| 14 | 10 | 1000 | 0.241 | 0.344 | 0.084 | 0.103 | 0.157 | − | + |
| 15 | 20 | 1000 | 0.255 | 0.411 | 0.094 | 0.156 | 0.161 | + | + |
| 16 | 50 | 1000 | 0.225 | 0.579 | 0.085 | 0.354 | 0.140 | + | + |

A type: Nucleoprotein of influenza A
B type: Nucleoprotein of influenza B
Observation of line: Line $n_{t1}$ is observed with a fluorescence reader. Line $n_{t2}$ is visually observed.

Example 2

Quantification of Target Substances

Calibration curves for each of the influenza A nucleoprotein and the influenza B nucleoprotein were prepared based on the results of Example 1 shown in Table 2. Then, two samples A and B (body fluids) were collected and subjected to one-time detection using the device shown above based on the calibration curves. As a result, for the sample A, the ($I_1-I_c$) value was 0.216, while the ($I_c-I_2$) value was 0.002. For the sample B, the ($I_1-I_c$) value was 0.005, while the ($I_c-I_2$) value was 0.044. From the results, the sample A was determined to contain the influenza A nucleoprotein in the concentration of 27 ng/mL, and the sample B was determined to contain the influenza B nucleoprotein in the concentration of 246 ng/mL. The components in the samples were quantified using another method (ELISA method). The results well agreed with the above results. The results show that the present invention allows quantitative detection with high accuracy.

In addition, the calibration curves were prepared using peak areas instead of the peak intensity differences, and quantitative measurement was performed. As a result, it was found that the accuracy of the quantitative detection further increased.

Preparation Example 4 (Preparation of Light Absorbing Silica Nanoparticles)

In 1 mL dimethyl formamide (DMF), 2.9 mg of 5-(and-6)-carboxyrhodamine 6G.succinimidyl ester (trade name, manufactured by EMP Biotech GmbH) was dissolved. Then, 1.3 μL of APS was added thereto and the reaction was carried out for 1 hour at room temperature (25° C.).

Next, 280 mg of AOT (aerosol OT) was added into 4 mL of heptane. Thereto, 40 μL of distilled water and 40 μL of 28% aqueous ammonia were added, and then the mixture was agitated very well. Thus, a reverse micellar liquid was prepared.

Next, 200 μL of the 5-(and-6)-carboxyrhodamine 6G/the silane coupling agent complex solution and 100 μL of the TEOS (tetraethyl orthosilicate) were added into the above mentioned reverse micellar liquid, the mixture was mixed very well at the room temperature, and then the reaction was performed for 24 hours.

Next, 4 mL of acetone was added thereinto, the mixture was mixed very well thereafter. And then a centrifugal separation was performed for 30 minutes with a gravitational acceleration of 22,000×g for removing a supernatant therefrom. Ethanol was added in an amount of 1 mL to the precipitated silica particles for dispersion, and the dispersion was centrifuged again at a gravitational acceleration of 22,000×g for 30 minutes. The washing operation was repeated twice additionally. Next, 1 mL of distilled water was added to the precipitated silica particles for dispersion, and then another centrifugal separation was performed for 30 minutes with a gravitational acceleration of 22,000×g. Further, the washing operation was repeated twice additionally, for removal of the unreacted TEOS, ammonia and others contained in the light absorbing silica particle dispersion.

Thus, 20.2 mg of light absorbing silica particles containing the 5-(and-6)-carboxyrhodamine 6G (average particle diameter: 238 nm) were obtained. Yield ratio: 74%
(Measurements of Absorption Spectrum and Molar Absorption Coefficient ε at Absorption Maximum Wavelength of Light Absorbing Silica Particles Containing 5-(and-6)-Carboxyrhodamine 6G)

With using an absorptiometer (manufactured by Molecular Devices Inc.) and a cell with a light path length of 1 cm, the absorption spectrum of an aqueous dispersion of the light absorbing silica particles containing the 5-(and-6)-carboxyrhodamine 6G and the molar absorption coefficient ε at the absorption maximum wavelength (546 nm) thereof were measured. The obtained ε at the wavelength of 532 nm was $1.1 \times 10^{10}$ $M^{-1}$ $cm^{-1}$.

Preparation Example 5 (Preparation of Complex Particles of Silica Particles and an Antibody)

Using the same process as in Preparation Example 2, 1 mL of colloid of 0.5 mg/mL complex particles was obtained, containing light absorbing silica particles containing 5-(and- 6)-carboxyrhodamine 6G (Preparation Example 6) and an antibody to nucleoprotein of the influenza B.

Example 3

A quick determination test for the influenza nucleoproteins was performed using the same method as in Example 1. Table 3 shows the results of the measurement and determination.

TABLE 3

| | Liquid mixture composition | | Measured values [a.u.] | | | | | Observation of lines | |
|---|---|---|---|---|---|---|---|---|---|
| | A type | B type | Base $n_c$ | Line $n_{t1}$ | Line $n_{t2}$ | | | | |
| No. | [ng/mL] | [ng/mL] | ($I_c$) | ($I_1$) | ($I_2$) | $I_1 - I_c$ | $I_c - I_2$ | Line $n_{t1}$ | Line $n_{t2}$ |
| 1 | 0 | 0 | 0.251 | 0.261 | 0.244 | 0.010 | 0.007 | − | − |
| 2 | 10 | 0 | 0.241 | 0.328 | 0.233 | 0.087 | 0.008 | − | − |
| 3 | 20 | 0 | 0.238 | 0.397 | 0.234 | 0.159 | 0.004 | + | − |
| 4 | 50 | 0 | 0.252 | 0.663 | 0.247 | 0.411 | 0.005 | + | − |
| 5 | 0 | 200 | 0.248 | 0.259 | 0.214 | 0.011 | 0.034 | − | − |
| 6 | 10 | 200 | 0.233 | 0.344 | 0.204 | 0.111 | 0.029 | − | − |
| 7 | 20 | 200 | 0.251 | 0.415 | 0.226 | 0.164 | 0.025 | + | − |
| 8 | 50 | 200 | 0.224 | 0.616 | 0.189 | 0.392 | 0.035 | + | − |
| 9 | 0 | 500 | 0.268 | 0.277 | 0.199 | 0.009 | 0.069 | − | + |
| 10 | 10 | 500 | 0.261 | 0.342 | 0.188 | 0.081 | 0.073 | − | + |
| 11 | 20 | 500 | 0.256 | 0.449 | 0.195 | 0.193 | 0.061 | + | + |
| 12 | 50 | 500 | 0.265 | 0.667 | 0.195 | 0.402 | 0.070 | + | + |
| 13 | 0 | 1000 | 0.241 | 0.25 | 0.127 | 0.009 | 0.114 | − | + |
| 14 | 10 | 1000 | 0.262 | 0.374 | 0.141 | 0.112 | 0.121 | − | + |
| 15 | 20 | 1000 | 0.236 | 0.409 | 0.12 | 0.173 | 0.116 | + | + |
| 16 | 50 | 1000 | 0.249 | 0.63 | 0.128 | 0.381 | 0.121 | + | + |

The results show that on the test line for the influenza A, the difference ($I_1-I_c$) between the peak fluorescence intensity of the line and the base-line fluorescence intensity for the sample containing 10 ng/mL or more of the influenza A nucleoprotein was significantly larger than the value for the sample containing no influenza A nucleoprotein. In the observation with the fluorescence reader, the detection limit was 20 ng/mL. It is apparent, therefore, that the present detection method has higher sensitivity.

Similarly, on the test line for the influenza B, the difference ($I_c-I_2$) between the base-line fluorescence intensity and the peak fluorescence intensity of the line for the sample containing 200 ng/mL or more of the influenza B nucleoprotein was significantly larger than the value for the sample containing no influenza B nucleoprotein. In the visual observation, the detection limit was 500 ng/mL. It is apparent, therefore, that the present detection method has higher sensitivity.

These results show that the present detection method allows the detection of two items at once by a single measurement and has higher sensitivity than observation with a fluorescence reader or visual observation.

Preparation Example 6 (Preparation of Fluorescent Silica Nanoparticles)

In 1 mL dimethyl formamide (DMF), 3.5 mg of ATTO532-NHS ester (trade name, manufactured by ATTO-TEC GmbH) was dissolved. Then, 1.3 μL of APS was added thereto and the reaction was carried out for 1 hour at room temperature (25° C.).

600 μL of the resulting reaction liquid was admixed with 140 mL of ethanol, 6.5 mL of TEOS, 35 mL of distilled water, and 15.5 mL of 28% by mass ammonia water, and the reaction was allowed to occur at room temperature for 24 hours.

The reaction solution was centrifuged at a gravitational acceleration of 15,000×g for 30 minutes, and the supernatant was removed. 4 mL of distilled water was added to the precipitated silica particles for dispersion, and the dispersion was centrifuged again at a gravitational acceleration of 15,000×g for 20 minutes. Further, the washing operation was repeated twice additionally, for removal of the unreacted TEOS, ammonia and others contained in the silica nanoparticle dispersion. Thus, 1.47 g of silica nanoparticles having an average particle diameter of 238 nm were obtained. Yield ratio: about 83%

Preparation Example 7 (Preparation of Complex Particles of Silica Particles and an Antibody)

Using the same process as in Preparation Example 2, 1 mL of colloid of 0.5 mg/mL complex particles was obtained, containing fluorescent silica particles containing ATTO532 and anti-norovirus GI monoclonal antibody (manufactured by Furukawa Electric Co., Ltd.).

Preparation Example 8 (Preparation of Light Absorbing Silica Nanoparticles)

First, 3.3 mg of 5-(and-6)-carboxytetramethylrhodamine, Succinimidyl Ester (produced by Molecular Probes) was dissolved in 1 mL of dimethylformamide (DMF). Next, 1.4 μL of APS (3-aminopropyltriethoxysilane) was added thereinto, a reaction was performed for one hour at a room temperature (23° C.) thereafter. Thus, a solution of the TAMRA/the silane coupling agent complex was obtained.

Next, 280 mg of AOT (aerosol OT) was added into 4 mL of heptane. Thereto, 40 μL of distilled water and 40 μL of 28% aqueous ammonia were added, and then the mixture was agitated very well. Thus, a reverse micellar liquid was prepared.

Next, 200 μL of the TAMRA/silane coupling agent complex solution and 100 μL of TEOS (tetraethyl orthosilicate) were added into the above mentioned reverse micellar liquid, the mixture was mixed very well at room temperature, and then the reaction was performed for 24 hours.

Next, 4 mL of acetone was added thereinto, the mixture was mixed very well thereafter. And then a centrifugal separation was performed for 30 minutes with a gravitational acceleration of 22,000×g for removing a supernatant therefrom. Ethanol was added in an amount of 1 mL to the precipitated silica particles for dispersion, and the dispersion was centrifuged again at a gravitational acceleration of 22,000×g for 30 minutes. The washing operation was repeated twice additionally. Next, 1 mL of distilled water was added to the precipitated silica particles for dispersion, and then another centrifugal separation was performed for 30 minutes with a gravitational acceleration of 22,000×g. Further, the washing operation was repeated twice additionally, for removal of the unreacted TEOS, ammonia and others contained in the light absorbing silica particle dispersion.

Thus, 18.0 mg of light absorbing silica particles (average particle diameter: 211 nm) containing TAMRA were obtained. Yield ratio: 66%

(Measurements of Absorption Spectrum and Molar Absorption Coefficient ε at Absorption Maximum Wavelength of Colloidal Silica Particles Containing TAMRA)

With using an absorptiometer (manufactured by Molecular Devices Inc.) and a cell with a light path length of 1 cm, the absorption spectrum of an aqueous dispersion of the colloidal silica particles containing the TAMRA and the molar absorption coefficient ε at the absorption maximum wavelength (546 nm) thereof were measured. The obtained ε at the wavelength of 660 nm was $1.6 \times 10^{10}$ $M^{-1}$ $cm^{-1}$.

Preparation Example 9 (Preparation of Complex Particles of Silica Particles and Antibody)

Using the same process as in Preparation Example 2, 1 mL of colloid of 0.5 mg/mL complex particles was obtained, containing light absorbing silica particles containing TAMRA and anti-norovirus GII monoclonal antibody (manufactured by Furukawa Electric Co., Ltd.).

Example 4

The colloid of the complex particles of the fluorescent silica particles and the antibody that had been obtained from Preparation Example 7 (240 μL), the complex particles of the light absorbing silica particles and the antibody that had been obtained from Preparation Example 9 (100 μL) and 50 mM $KH_2PO_4$ (pH 7.0, 460 μL) were admixed with each other. The resulting mixture (800 μL) was uniformly coated on Glass Fiber Conjugate Pad (GFCP, manufactured by MILLIPORE) (8×150 mm). After drying overnight at room temperature under reduced pressure in a desiccator, a conjugate pad containing the complex particles which had been obtained from Preparation Examples was manufactured.

Next, an antibody immobilizing membrane was produced as follows.

At the about 9 mm from the end of the membrane (length: 25 mm, trade name: Hi-Flow Plus180 membrane, manufactured by MILLIPORE), a solution ((50 mM $KH_2PO_4$, pH 7.0)+5% sucrose) containing an anti-mouse antibody to norovirus GI (manufactured by Furukawa Electric Co., Ltd.) in an amount of 1 mg/mL was coated in a coating amount of 0.75 μL/cm to give a test line for the norovirus GI with width of about 1 mm.

Subsequently, as a test line for the norovirus GII with width of about 1 mm, a solution ((50 mM $KH_2PO_4$, pH 7.0)+5% sucrose) containing an anti-mouse norovirus GII antibody (manufactured by Furukawa Electric Co., Ltd.) in an amount of 1 mg/mL was coated in a coating amount of 0.75 μL/cm. A distance d between the test line for the norovirus GI and the test line for the norovirus GII was set to 3 mm.

Subsequently, as a control line with width of about 1 mm, a solution ((50 mM $KH_2PO_4$, pH 7.0), sugar free) containing a goat anti-mouse IgG antibody (AKP Goat anti-mouse IgG Antibody, manufactured by BioLegend) in an amount of 1 mg/mL was coated in a coating amount of 0.75 μL/cm followed by drying for 30 min at 50° C. A distance between the test line for the norovirus GII and the control line was set to 3 mm.

The sample pad (Glass Fiber Conjugate Pad (GFCP), manufactured by MILLIPORE), the above-described conjugate pad, the antibody immobilizing membrane, and the absorption pad (Cellulose Fiber Sample Pad (CFSP), manufactured by MILLIPORE) were assembled in this order on a backing sheet (trade name; AR9020, manufactured by Adhesives Research). The membrane was configured in such an orientation that the test line for the norovirus GI was on the conjugate pad side, while the control line was on the absorption pad side.

Quick Determination of Norovirus Antigens

According to the composition shown in Table 4, a liquid mixture of the norovirus GI antigen (VLP GI/1) and the norovirus GII antigen (VLP GII/4) was prepared. Subsequently, 100 μL of the liquid mixture was added dropwise to the sample pad part of the test strip. After 15 minutes, the measurement was performed with the detector of Production Example, and the test line for the norovirus GI was observed with a fluorescence reader, while the test line for the norovirus GII was visually observed.

TABLE 4

| | Liquid mixture composition | | Measured values [a.u.] | | | | | Observation of lines | |
|---|---|---|---|---|---|---|---|---|---|
| | VLP GI/1 | VLP GII/4 | Base $n_c$ | Line $n_{t1}$ | Line $n_{t2}$ | | | | |
| No. | [ng/mL] | [ng/mL] | ($I_c$) | ($I_1$) | ($I_2$) | $I_1 - I_c$ | $I_c - I_2$ | Line $n_{t1}$ | Line $n_{t2}$ |
| 1 | 0 | 0 | 0.274 | 0.282 | 0.262 | 0.008 | 0.012 | − | − |
| 2 | 0.1 | 0 | 0.261 | 0.322 | 0.252 | 0.061 | 0.009 | − | − |
| 3 | 0.2 | 0 | 0.288 | 0.419 | 0.277 | 0.131 | 0.011 | + | − |
| 4 | 0.5 | 0 | 0.281 | 0.601 | 0.268 | 0.320 | 0.013 | + | − |
| 5 | 0 | 1 | 0.257 | 0.267 | 0.231 | 0.010 | 0.026 | − | − |
| 6 | 0.1 | 1 | 0.265 | 0.336 | 0.237 | 0.071 | 0.028 | − | − |
| 7 | 0.2 | 1 | 0.255 | 0.384 | 0.231 | 0.129 | 0.024 | + | − |
| 8 | 0.5 | 1 | 0.278 | 0.61 | 0.246 | 0.332 | 0.032 | + | − |
| 9 | 0 | 2.5 | 0.281 | 0.293 | 0.224 | 0.012 | 0.057 | − | + |
| 10 | 0.1 | 2.5 | 0.257 | 0.331 | 0.202 | 0.074 | 0.055 | − | + |

TABLE 4-continued

| | Liquid mixture composition | | Measured values [a.u.] | | | | | Observation of lines | |
|---|---|---|---|---|---|---|---|---|---|
| | VLP GI/1 | VLP GII/4 | Base $n_c$ | Line $n_{t1}$ | Line $n_{t2}$ | | | | |
| No. | [ng/mL] | [ng/mL] | ($I_c$) | ($I_1$) | ($I_2$) | $I_1 - I_c$ | $I_c - I_2$ | Line $n_{t1}$ | Line $n_{t2}$ |
| 11 | 0.2 | 2.5 | 0.29 | 0.438 | 0.226 | 0.148 | 0.064 | + | + |
| 12 | 0.5 | 2.5 | 0.266 | 0.62 | 0.207 | 0.354 | 0.059 | + | + |
| 13 | 0 | 5 | 0.279 | 0.287 | 0.17 | 0.008 | 0.109 | − | + |
| 14 | 0.1 | 5 | 0.259 | 0.318 | 0.143 | 0.059 | 0.116 | − | + |
| 15 | 0.2 | 5 | 0.286 | 0.431 | 0.185 | 0.145 | 0.101 | + | + |
| 16 | 0.5 | 5 | 0.281 | 0.652 | 0.168 | 0.371 | 0.113 | + | + |

The results show that on the test line for the norovirus GI, the difference ($I_1-I_c$) between the peak fluorescence intensity of the line and the base-line fluorescence intensity for the sample containing 0.1 ng/mL or more of VLP GI/1 was significantly larger than the value for the sample containing no VLP GI/1. In the observation with the fluorescence reader, the detection limit was 0.2 ng/mL. It is apparent, therefore, that the present detection method has higher sensitivity.

Similarly, on the test line for the norovirus GII, the difference ($I_c-I_2$) between the base-line fluorescence intensity and the peak fluorescence intensity of the line for the sample containing 1 ng/mL or more of VLP GII/4 was significantly larger than the value for the sample containing no VLP GII/4. In the visual observation, the detection limit was 2.5 ng/mL. It is apparent, therefore, that the present detection method has higher sensitivity.

These results show that the present detection method allows the detection of two items at once by a single measurement and has higher sensitivity than observation with a fluorescence reader or visual observation.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Target substance (Analyte substance)
  1A First target substance
  1B Second target substance
2 Fluorescent labeling unit
  2a Fluorescent particulates
  2b Binding substance
3 Light absorbing labeling unit
  3a Light absorbing fine particulates
  3b Binding substance
4, 5 Test use capturing substance
6 Casing
  61 Detection opening
  62 Opening for introducing analyte
  6a Upper casing
  6b Lower casing
  8a Sample pad
  8b Conjugate pad
  8c Membrane
  8d Absorption pad
  8e Backing sheet
7 Reference use capturing substance
10 Test piece (Test strip)
100 Long test stick
$n_{t1}$ First test area (Test line)
$n_{t2}$ Second test area (Test line)
$n_r$ Reference area (Reference line)
L Lateral flow direction
S Analyte liquid
20 Detection part
21 Main detection unit
  21a Sample inlet
  21b Sample guide
23 Wiring
25 Personal computer (Control unit)
27 Optical receiver
28 Receiver lens
29 Light irradiator

The invention claimed is:

1. An immunochromatography for multi-target substance detection, comprising steps of:
applying, to a test piece having fluorescent particles and light absorbing particles as labeling particles, a liquid sample suspected of containing target substances A and B, so that the fluorescent particles and the light absorbing particles are allowed to flow; and
detecting and measuring fluorescence and detecting light absorption with a single scan with a detection device,
wherein the fluorescence is derived from the fluorescent particles captured in a test area of the test piece, and the light absorption is derived from the light absorbing particles captured in another test area of the test piece,
wherein the detection device comprises a detection unit for detecting fluorescence and light absorption with a single scan, and a control unit for controlling the detection unit,
wherein the fluorescent particles and the light absorbing particles are such that the fluorescent particles have a fluorescence excitation wavelength ($\lambda_1$), the light absorbing particles have an absorption wavelength ($\lambda_2$), the fluorescence excitation wavelength ($\lambda_1$) and the absorption wavelength ($\lambda_2$) are in a wavelength region of 300 nm to 800 nm, the target substance A is captured by the fluorescent particles in a test area $n_{t1}$, the target substance B is captured by the light absorbing particles in a test area $n_{t2}$, and the target substance A and the target substance B are different from each other,
wherein the test area $n_{t1}$ where the fluorescent particles are captured and the test area $n_{t2}$ where the light absorbing particles are captured each are provided at different positions, and
wherein the control unit of the detection device commands the detection unit to scan the test piece and to detect and measure with a single scan, an intensity of emitted fluorescence from the test area $n_{t1}$, an intensity of reflected light from the test area $n_{t2}$, and an intensity of reflected light from a non-test area which is other than the test areas $n_{t1}$ and $n_{t2}$.

2. The immunochromatography according to claim 1, wherein the detection device detects the target substances by the fact that the intensity of reflected light from the test area $n_{t1}$ where the fluorescent particles are captured is higher than the intensity of reflected light from the non-test area and by the fact that the intensity of reflected light from the test area $n_{t2}$ where the light absorbing particles are captured is lower than the intensity of reflected light from the non-test area.

3. The immunochromatography according to claim 1, wherein the fluorescent particles are fluorescent silica particles, and wherein the light absorbing particles are gold colloid particles, colored silica particles, or colored latex particles.

4. The immunochromatography according to claim 1, wherein the distance between the test areas $n_{t1}$ and $n_{t2}$ is in the range of from 1 mm to 10 mm.

5. The immunochromatography according to claim 1, wherein the target substances are quantified from an area of a peak corresponding to the fluorescence excitation wavelength and/or an area of a peak corresponding to the light absorption wavelength.

6. The immunochromatography according to claim 1, wherein the intensity of reflected light from the test area $n_{t1}$ where the fluorescent particles are captured, the intensity of reflected light from the test area $n_{t2}$ where the light absorbing particles are captured, and the intensity of reflected light from the non-test area are all detected by a single optical receiver provided with the detection unit.

7. The immunochromatography according to claim 1, wherein for the sample suspected of containing the target substances A and B, the presence of the target substance A is determined by the fact that the intensity of reflected light from the test area $n_{t1}$ is higher than the intensity of reflected light from the non-test area, the presence of the target substance B is determined by the fact that the intensity of reflected light from the test area $n_{t2}$ is lower than the intensity of reflected light from the non-test area, the absence of both substances is determined by the fact that the intensity of reflected light from the test area $n_{t1}$, the intensity of reflected light from the test area $n_{t2}$, and the intensity of reflected light from the non-test area are at substantially the same level, and the presence of both substances is determined by the fact that the intensity of reflected light from the test area $n_{t1}$ is higher than the intensity of reflected light from the non-test area, and the fact that the intensity of reflected light from the test area $n_{t2}$ is lower than the intensity of reflected light from the non-test area.

* * * * *